United States Patent [19]
Kato

[11] Patent Number: 5,893,968
[45] Date of Patent: Apr. 13, 1999

[54] METHOD AND APPARATUS FOR MEASURING COMBUSTIBLE GAS COMPONENT BY BURNING THE COMPONENT

[75] Inventor: Nobuhide Kato, Aichi-ken, Japan

[73] Assignee: NGK Insulators, Ltd., Japan

[21] Appl. No.: 09/083,053

[22] Filed: May 22, 1998

Related U.S. Application Data

[62] Division of application No. 08/611,771, Mar. 6, 1996.

[30] Foreign Application Priority Data

Mar. 9, 1995 [JP] Japan ................................. 7-49504

[51] Int. Cl.$^6$ .................................................. G01N 27/26
[52] U.S. Cl. ................ 205/784.5; 205/782; 205/783.5; 205/784; 205/785.5; 205/787; 422/94; 422/98; 73/23.31
[58] Field of Search ................... 205/784.5, 782, 205/783.5, 784, 785.5, 787; 73/23.31; 422/94, 98

[56] References Cited

U.S. PATENT DOCUMENTS

| | | | |
|---|---|---|---|
| 4,158,166 | 6/1979 | Isenberg | 204/425 |
| 4,199,425 | 4/1980 | Sinkevitch | 204/195 |
| 4,441,981 | 4/1984 | Okamoto et al. | 204/426 |
| 4,759,827 | 7/1988 | Okada et al. | 205/784.5 |
| 5,049,254 | 9/1991 | Logothetis et al. | 204/425 |
| 5,281,313 | 1/1994 | Visser et al. | 205/784.5 |
| 5,505,837 | 4/1996 | Friese et al. | 204/425 |
| 5,580,440 | 12/1996 | Ueno et al. | 205/784.5 |

FOREIGN PATENT DOCUMENTS

| | | |
|---|---|---|
| 0060944 | 9/1982 | European Pat. Off. . |
| 0678740 | 10/1995 | European Pat. Off. . |
| 3742014 | 6/1989 | Germany . |

Primary Examiner—Bruce F. Bell
Attorney, Agent, or Firm—Parkhurst & Wendel, L.L.P

[57] ABSTRACT

An apparatus for measuring a combustible gas component of a subject gas in an external subject gas space, including a first processing zone communicating with the subject gas space, 58), a second processing zone communicating with the first processing zone, and a first and a second pumping cell exposed to the first and second processing zones, respectively, each cell including an oxygen ion conductive solid electrolyte layer and a pair of electrodes one of which is exposed to the first or second processing zone, wherein the first pumping cell pumps oxygen out of the first processing zone to control oxygen partial pressure in the first processing zone at a value at which the combustible gas component cannot be burned, while the second pumping cell pumps oxygen into the second processing zone to thereby burn the combustible gas component in the second processing zone, and the concentration of the combustible gas component is determined based on a current flowing or a voltage between the electrodes of the second pumping cell.

6 Claims, 12 Drawing Sheets

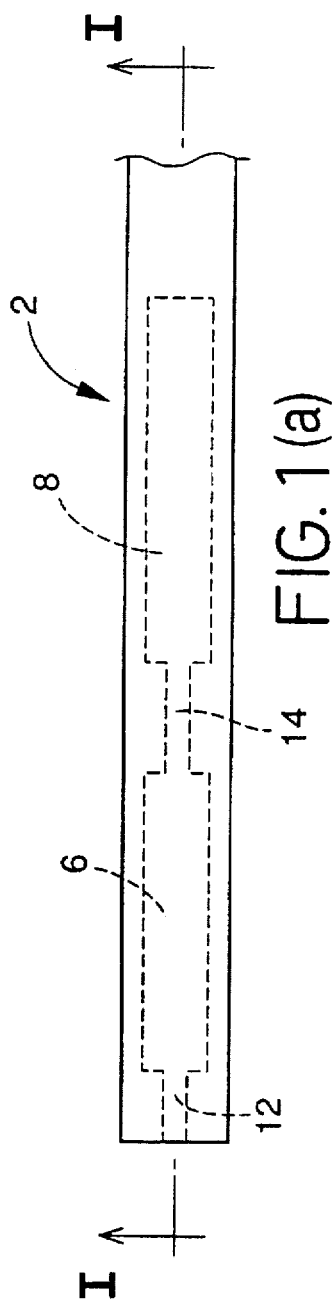
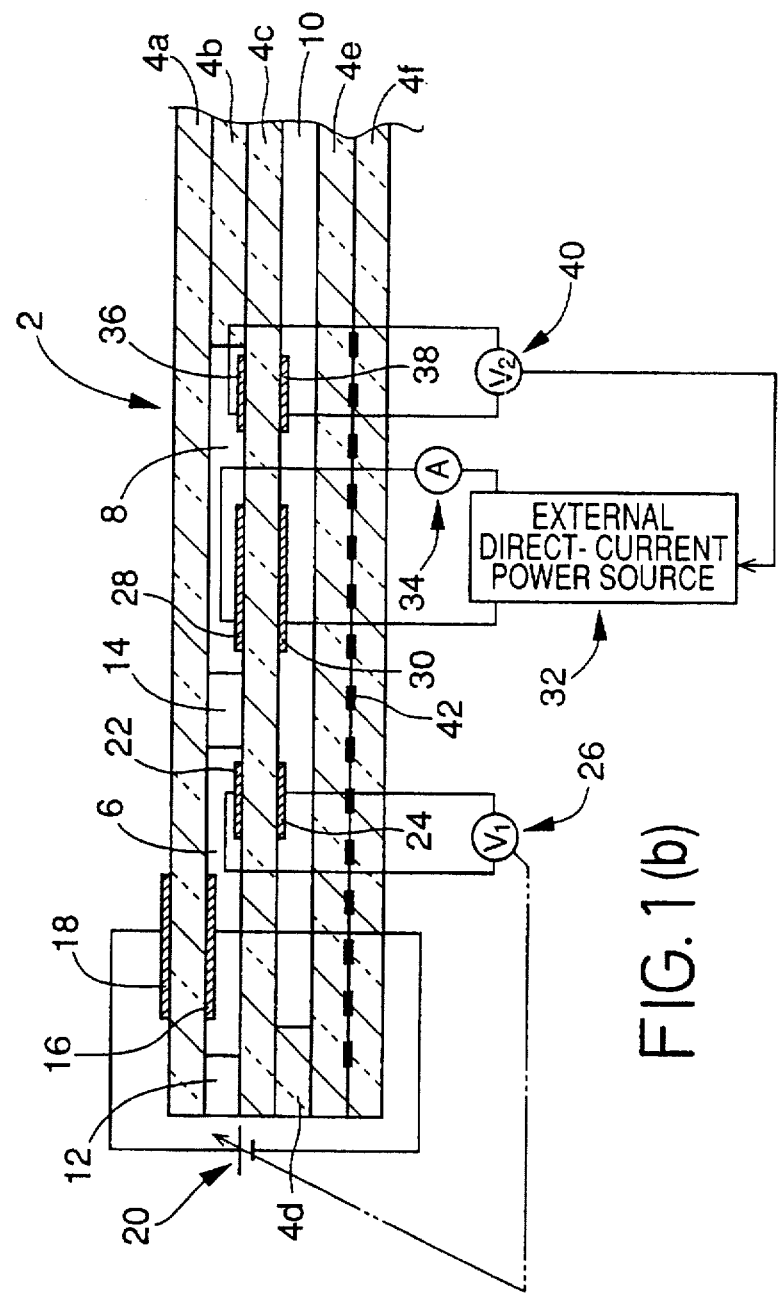

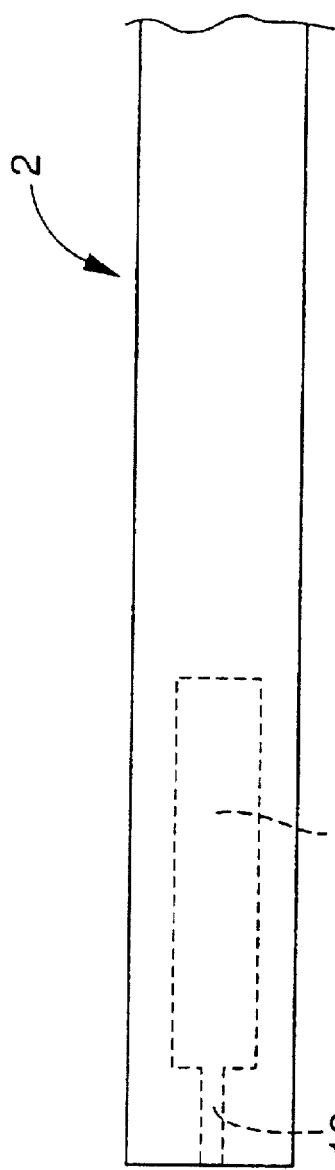
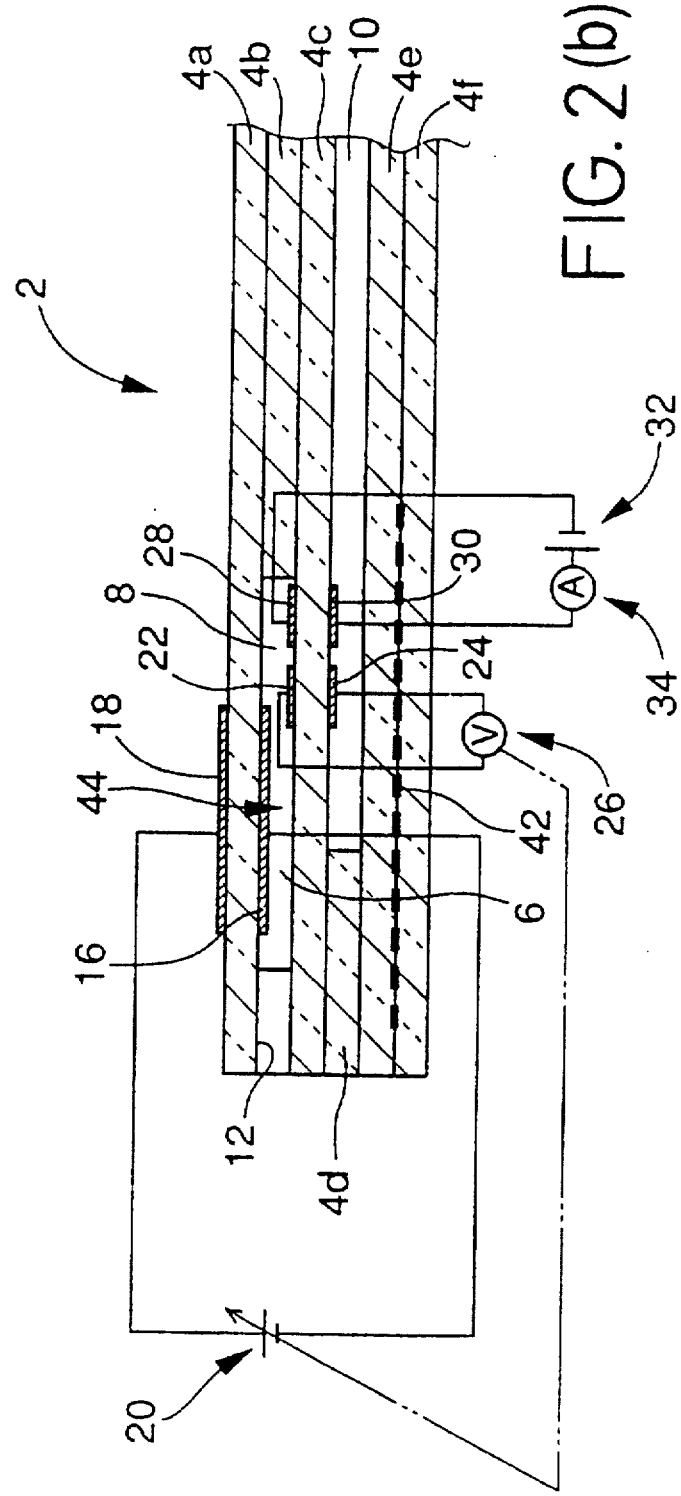
FIG. 2(a)
FIG. 2(b)

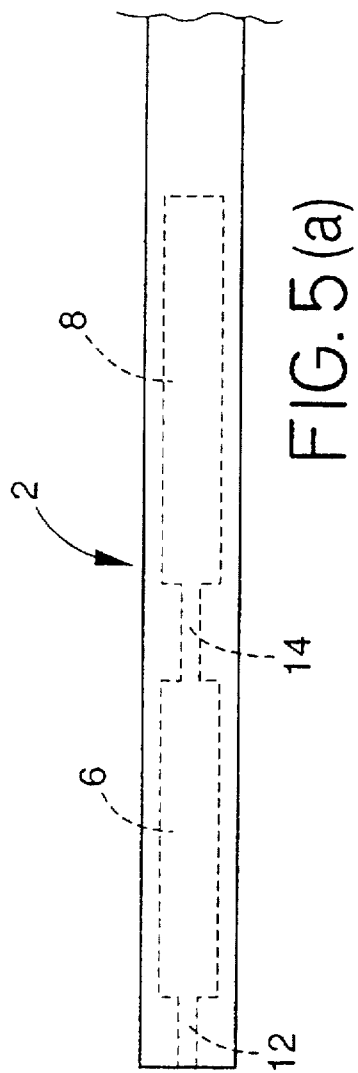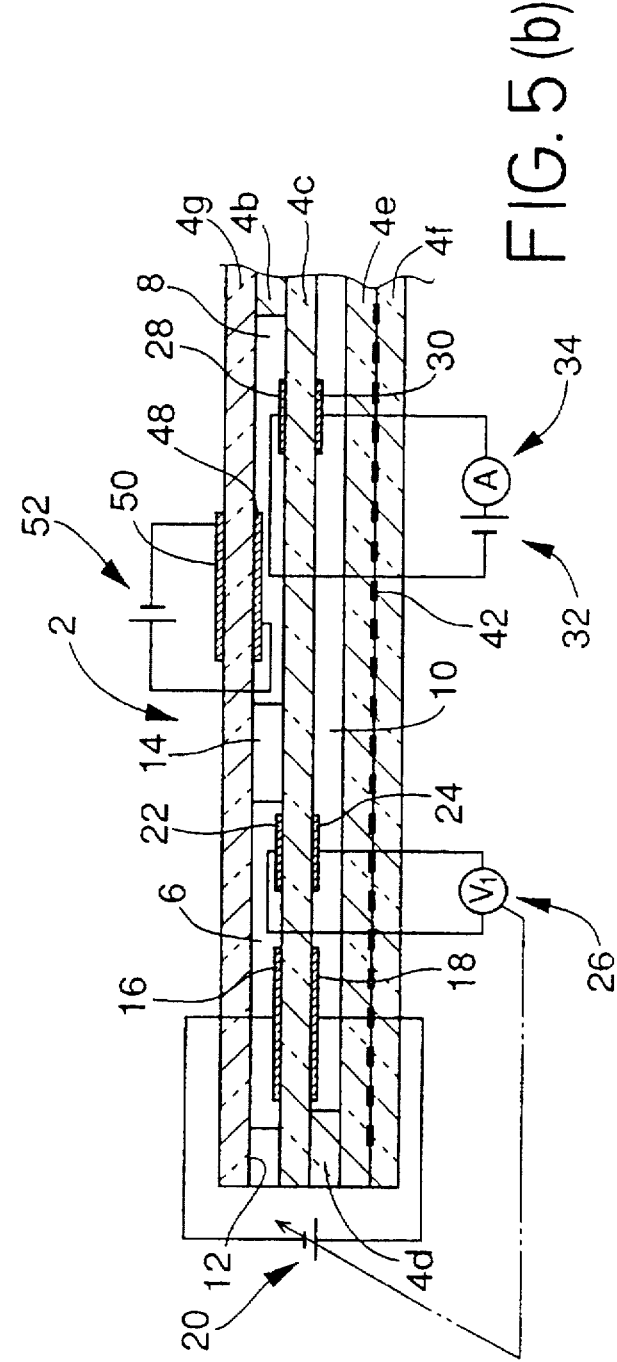

METHOD AND APPARATUS FOR MEASURING COMBUSTIBLE GAS COMPONENT BY BURNING THE COMPONENT

This is a Division of application Ser. No. 08/611,771 filed Mar. 6, 1996, pending.

BACKGROUND OF THE INVENTION

1. Field of the Invention

The present invention relates in general to a method and an apparatus for measuring combustible gas components, in particular, for measuring the concentrations of combustible gas components included in combustion gases emitted from internal combustion engines, external combustion engines, combustion furnaces and the like which are operated with a heavy oil, a light oil, a gasoline or a natural gas. More particularly, this invention is concerned with such method and apparatus that permit accurate measurement or determination of the concentration of hydrocarbon (HC) included in a subject gas (combustion gas) which also includes hydrogen ($H_2$) and carbon monoxide (CO).

2. Discussion of the Related Art

In the field of measuring combustible gas components in a subject gas such as a combustion gas as indicated above, there is known a so-called "contact burning" type gas sensor which utilizes platinum (Pt) as an oxidizing catalyst This contact burning type gas sensor is adapted to oxidize and burn the combustible gas components of the subject gas in contact with a platinum resistor wire, and measure the concentration of the combustible gas components according to an electric signal indicative of the electrical resistance of the platinum resistor wire, which varies with a rise of the temperature of the platinum resistor wire due to heat generated by the burning of the combustible gas components.

In this contact burning type gas sensor wherein the combustible gas components are burned in contact with the platinum resistor wire, it is essential that the subject gas include oxygen. Therefore, this gas sensor is not capable of dealing with subject gases whose oxygen concentration is insufficient for burning the combustible gas components. For instance, the gas sensor is not capable of dealing with combustion gases produced as a result of combustion of a fuel-rich air-fuel mixture whose air/fuel ratio is smaller than the stoichiometric value. Where the subject gas includes $H_2$, CO and HC as the combustible gas components, the output of the gas sensor represents the total concentration of all the combustible gas components. Thus, the gas sensor does not permit the determination of the concentration of HC only, in the presence of $H_2$ and CO.

Various gas sensors of metal oxide semiconductor type are also proposed The metal oxide semiconductor type gas sensor utilizes a sintered body of a metal oxide such as tin oxide and zinc oxide, which exhibits properties of an N-type semiconductor The electrical resistance of such a metal oxide semiconductor varies as the combustible gas components of the subject gas are adsorbed on the metal oxide semiconductor. The concentration of the combustible gas components is determined on the basis of a change in the electrical resistance of the metal oxide semiconductor. However, the output of this type of gas sensor is influenced by oxygen and humidity, and the gas sensor is not capable of selectively obtaining the concentration of HC, due to an influence of the other combustible gas components.

U.S. Pat. No. 4,158,166 discloses a sensor for measuring the concentration of combustible gas components, which uses an electrochemical oxygen pumping cell constituted by an oxygen ion conductive solid electrolyte body and a pair of electrodes. This gas sensor is adapted to burn the combustible gas components and determine the concentration of the combustible gas components on the basis of an electric current (pumping current) flowing through the pumping cell. However, this gas sensor is considerably influenced by the existence of oxygen. That is, the subject gas that can be handled by this gas sensor is limited to a combustible gas atmosphere in which the amount of combustibles or fuel components is larger than the amount of oxygen. If the amount of oxygen is almost equal to the amount of the combustible gas components, the combustible gas components will be oxidized by reaction with oxygen in the subject gas, without a supply of oxygen from another source by an oxygen pumping action of the oxygen pumping cell. As a result, the pumping current of the pumping cell does not accurately reflect the concentration of the combustible gas components. Thus, the measurement of the concentration of the combustible gas components on the basis of the pumping current is difficult.

SUMMARY OF THE INVENTION

The present invention was developed in an effort to solve the drawbacks of the known method and apparatus for measuring the combustible gas components It is therefore a first object of the present invention to provide a method by which the concentration of a combustible gas component of a subject gas can be accurately measured without an influence of the oxygen concentration of the subject gas.

It is a second object of this invention to provide an apparatus suitable for practicing the method of the invention.

It is an optional object of this invention to provide a method and an apparatus which permit a high degree of sensitivity to HC as a combustible gas component, with a minimum influence of CO and $H_2$.

According to a first aspect of the present invention, there is provided a method of measuring a combustible gas component of a subject gas, comprising the steps of: (a) introducing the subject gas into a first processing zone under a predetermined diffusion resistance; (b) energizing a first electrochemical oxygen pumping cell to perform an oxygen pumping action for pumping oxygen out of the first processing zone to thereby control an oxygen partial pressure of an atmosphere within the first processing zone to a predetermined value at which the combustible gas component cannot be substantially burned; (c) introducing the atmosphere from the first processing zone into a second processing zone under a predetermined diffusion resistance; (d) energizing a second electrochemical oxygen pumping cell to perform an oxygen pumping action for pumping oxygen into the second processing zone to thereby burn the combustible gas component present in an atmosphere within the second processing zone; and (e) detecting one of a pumping current flowing through the second electrochemical oxygen pumping cell and a voltage between electrodes of the second electrochemical oxygen pumping cell during energization of the second electrochemical oxygen pumping cell, and obtaining an amount of the combustible gas component in the subject gas, on the basis of the detected pumping current or voltage.

In the method of the present invention described above, the concentration of the combustible gas component present in the subject gas can be suitably measured without an influence of the oxygen included in the subject gas.

According to a first preferred feature of the present invention, the method is practiced to deal with the subject gas which includes carbon monoxide (CO), hydrogen ($H_2$) and hydrocarbon (HC) as combustible gas components. In this case, the method further comprises a step of burning the carbon monoxide and hydrogen before the subject gas is introduced into the first processing zone, and the concentration of the hydrocarbon in the subject gas is determined on the basis of the detected pumping current or voltage of the second electrochemical oxygen pumping cell.

Since the carbon monoxide and hydrogen are burned before the subject gas is introduced into the first processing zone, the HC concentration can be determined without an influence of CO and $H_2$. In other words, the present method is capable of determining the HC concentration with high sensitivity, and therefore has a remarkable industrial significance.

According to a second preferred feature of the invention, the method is practiced to deal with the subject gas which includes hydrogen and hydrocarbon as combustible gas components. In this instance, the method further comprises a step of energizing a proton pump to perform a proton pumping action for pumping hydrogen out of the first and second processing zone, and the concentration of the hydrocarbon in the subject gas is determined on the basis of the detected pumping current or voltage of the electrochemical oxygen pumping cell. In this respect, it is noted that hydrogen may be produced according to a reaction $CO+H_2O \leftrightarrows CO_2+H_2$. The thus produced hydrogen is also pumped out by the proton pump.

According to a third preferred feature of the invention, the first and second electrochemical oxygen pumping cells are held at an elevated temperature by a suitable heater, so as to assure effective oxygen pumping actions.

According to a fourth preferred feature of the invention, the method further comprises a step of detecting the oxygen partial pressure of the atmosphere within the first processing zone, and a voltage of a variable-voltage power source to be applied to electrodes of the first electrochemical oxygen pumping cell is controlled on the basis of the detected oxygen partial pressure within the first processing zone, such that the detected oxygen partial pressure within the first processing zone is held at the predetermined value.

According to a fifth preferred feature of the invention, the oxygen partial pressure of the atmosphere within the first processing zone is held at $10^{-14}$ atm or lower, so as to inhibit the oxidization of HC, CO and $H_2$ included as combustible gas components in the atmosphere in the first processing zone.

According to a sixth preferred feature of the invention, the second electrochemical oxygen pumping cell performs the oxygen pumping action such that an amount of oxygen to be pumped into the second processing zone is not smaller than an amount which is substantially necessary to burn the combustible gas component, and such that a partial pressure of residual oxygen remaining in the second processing zone after burning of the combustible gas component is held at a predetermined value.

According to a seventh preferred feature of the invention, the residual oxygen partial pressure in the second processing zone is controlled to $1/100$ or smaller of the concentration of the combustible gas components included in the subject gas, so as to improve the accuracy of measurement of the appropriate combustible gas component.

The method according to the present invention may be suitably practiced by an apparatus constructed according to a second aspect of the present invention for measuring a combustible gas component of a subject gas, the apparatus comprising (a) a first processing zone communicating with an external subject gas space in which the subject gas exists; (b) first diffusion control means for introducing the subject gas from the external subject gas space into the first processing zone under a predetermined diffusion resistance; (c) a first electrochemical oxygen pumping cell including a first oxygen ion conductive solid electrolyte layer which partially defines the first processing zones and a first pair of electrodes which are disposed in contact with the first oxygen ion conductive solid electrolyte layer and one of which is exposed to the first processing zone, the first electrochemical oxygen pumping cell being energized to perform an oxygen pumping action for pumping oxygen out of the first processing zone to thereby control an oxygen partial pressure of an atmosphere within the first processing zone to a predetermined value at which the combustible gas component cannot be substantially burned; (d) a second processing zone communicating with the first processing zone; (e) second diffusion control means for introducing the atmosphere from the first processing zone into the second processing zone under a predetermined diffusion resistance; (f) a second electrochemical oxygen pumping cell including a second oxygen ion conductive solid electrolyte layer which partially defines the second processing zone, and a second pair of electrodes which are disposed in the second oxygen ion conductive solid electrolyte layer and one of which is exposed to the second processing zone, the second electrochemical oxygen pumping cell being energized to perform an oxygen pumping action for pumping oxygen into the second processing zone to thereby burn the combustible gas component present in an atmosphere within the second processing zone; and (g) detecting means for detecting one of a pumping current flowing through the second electrochemical oxygen pumping cell and a voltage between the second pair of electrodes, during energization of the second electrochemical oxygen pumping cell.

The present apparatus has substantially the same advantages as described above with respect to the method of the present invention.

According to a first preferred form of the apparatus of the present invention, the first and second processing zones, the first and second diffusion control means and the first and second electrochemical oxygen pumping cells are integrally provided in a sensing element, which includes the first and second oxygen ion conductive solid electrolyte layers as an integral part thereof.

According to one advantageous arrangement of the above first preferred form of the apparatus, the sensing element has a single generally elongate internal space communicating with the external subject gas space, and the internal space has a first portion which is adjacent to the first diffusion control means and which includes the first processing zone, and a second portion remote from the first diffusion control means and which includes the second processing zone. In this case, the first diffusion control means may be formed in the sensing element such that the first diffusion control means communicates at one end thereof with the first portion of the internal space, and is open at the other end to the external subject gas space.

According to a second advantageous arrangement of the above first preferred form of the apparatus, the sensing element has a first and a second internal cavity which provide the first and second processing zones, respectively, and the first internal cavity communicates with the external subject gas space, while the second internal cavity communicates with the first internal cavity. In this case, the first diffusion control means may be formed in communication with the first internal cavity and is open to the external subject gas space, while the second diffusion control means is formed between and in communication with the first and second internal cavities.

According to a second preferred form of the apparatus of the invention, there is provided a selective oxidizing catalyst which is capable of oxidizing carbon monoxide and hydrogen included as combustible gas components in the subject gas and is not capable of oxidizing hydrocarbon also included as a combustible gas component in the subject gas. The selective oxidizing catalyst is positioned relative to the first processing zone such that the subject gas is brought into contact with the selective oxidizing catalyst when the subject gas is introduced into the first processing zone.

The first and second oxygen ion conductive solid electrolyte layers of the first and second electrochemical oxygen pumping cells may consist of respective layers. Alternatively, a single oxygen ion conductive solid electrolyte layer may be used to function as the first and second oxygen ion conductive solid electrolyte layers of the two pumping cells.

According to a third preferred form of the present apparatus, there are provided first oxygen partial pressure detecting means for detecting the oxygen partial pressure of the atmosphere within the first processing zone, and a variable-voltage power source for applying a voltage between the first pair of electrodes of the first electrochemical oxygen pumping cell such that the voltage is controlled on the basis of the oxygen partial pressure detected by the first oxygen partial pressure detecting means, to thereby control the oxygen partial pressure of the atmosphere within the first processing zone.

According to a fourth preferred form of the apparatus, there is provided a power source for applying a voltage between the second pair of electrodes of the second electrochemical oxygen pumping cell such that an oxygen partial pressure of the atmosphere within the second processing zone is held at a predetermined constant value. In this case, second oxygen partial pressure detecting means may be provided for detecting an oxygen partial pressure of the atmosphere within the second processing zone. In this instance, the voltage to be applied between the second pair of electrodes may be determined such that the oxygen partial pressure detected by the second oxygen partial pressure detecting means is held at the predetermined constant value.

According to a fifth preferred form of the apparatus, there is provided a proton pump including a proton ion conductive solid electrolyte layer which partially defines the first processing zone, and a pair of proton pumping electrodes which are disposed in contact with the proton ion conductive solid electrolyte layer and one of which is exposed to the first processing zone. The proton pump is energized to perform a proton pumping action for pumping hydrogen out of the first processing zone.

According to a sixth preferred form of the apparatus, there is provided a proton pump including a proton ion conductive solid electrolyte layer which partially defines the second processing zone, and a pair of proton pumping electrodes which are disposed in contact with the proton ion conductive solid electrolyte layer and one of which is exposed to the second processing zone. The proton pump is energized to perform a proton pumping action for pumping hydrogen out of the second processing zone.

In the above fifth and sixth preferred forms of the apparatus, an aqueous gas converting catalyst may be provided for converting carbon monoxide in the first or second processing zone into hydrogen. This aqueous gas converting catalyst is located at the same position as or upstream of the proton pump as seen in a direction of diffusion from the first processing zone toward the second processing zone. For instance, the aqueous gas converting catalyst may be formed on the above-indicated one of the pair of proton pumping electrodes which is exposed to the first or second processing zone.

According to a seventh preferred form of the apparatus, the second processing zone includes the second diffusion control means. This second diffusion control means may consist of a porous layer formed on the above-indicated one of the second pair of electrodes which is exposed to the second processing zone. This electrode of the second electrochemical oxygen pumping cell may function as a catalyst for oxidizing the combustible gas component. Furthers this electrode may be formed of a porous cermet consisting of a ceramic material, and a metal capable of oxidizing the combustible gas component.

According to an eighth preferred form of the apparatus of the inventions there is provided heating means for heating the first and second electrochemical oxygen pumping cells to hold these pumping cells at a predetermined temperature for permitting the pumping cells to perform effective oxygen pumping actions.

BRIEF DESCRIPTION THE DRAWINGS

The above and optional objects, features, advantages, and technical and industrial significance of the present invention will be better understood by reading the following detailed description of presently preferred embodiments of the invention, when considered in conjunction with the accompanying drawings, in which:

FIG. 1(a) is a fragmentary plan view of a combustible gas component measuring apparatus constructed according to one embodiment of the present invention;

FIG. 1(b) is a fragmentary enlarged view in cross sectional taken along line I—I of FIG. 1(a);

Figure 3:
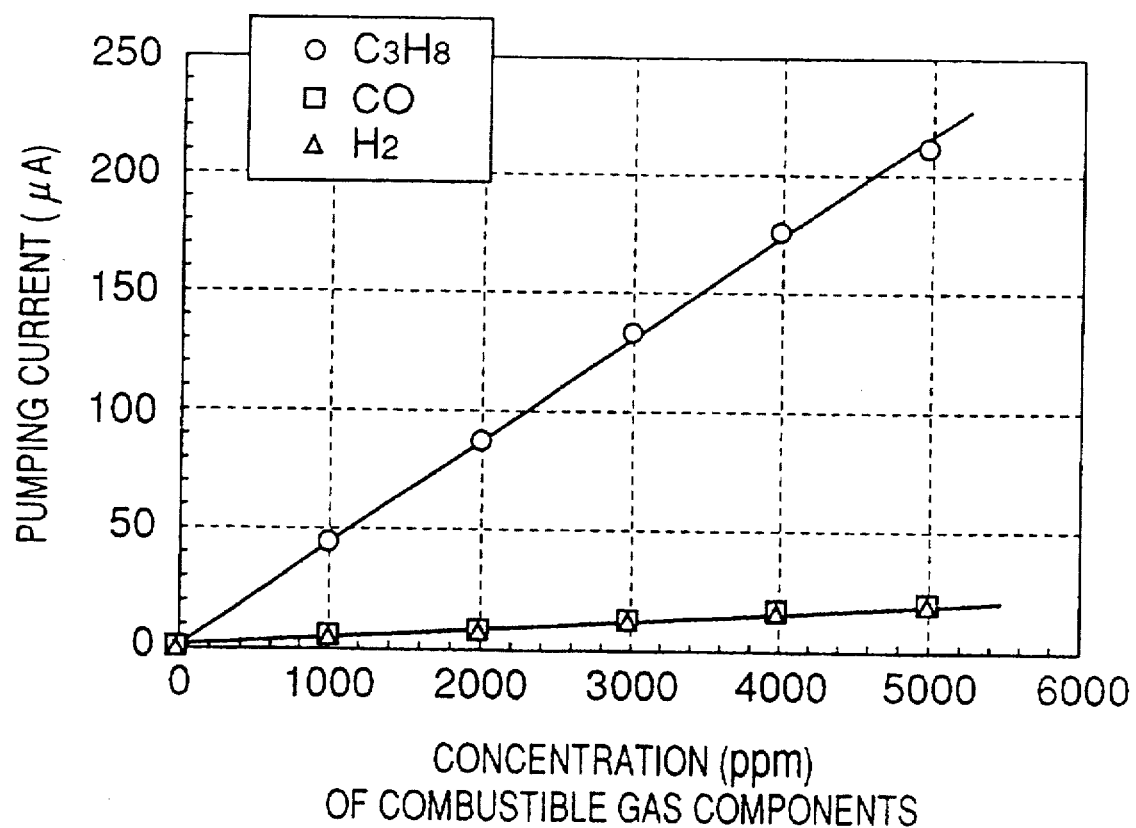
Figure 4:
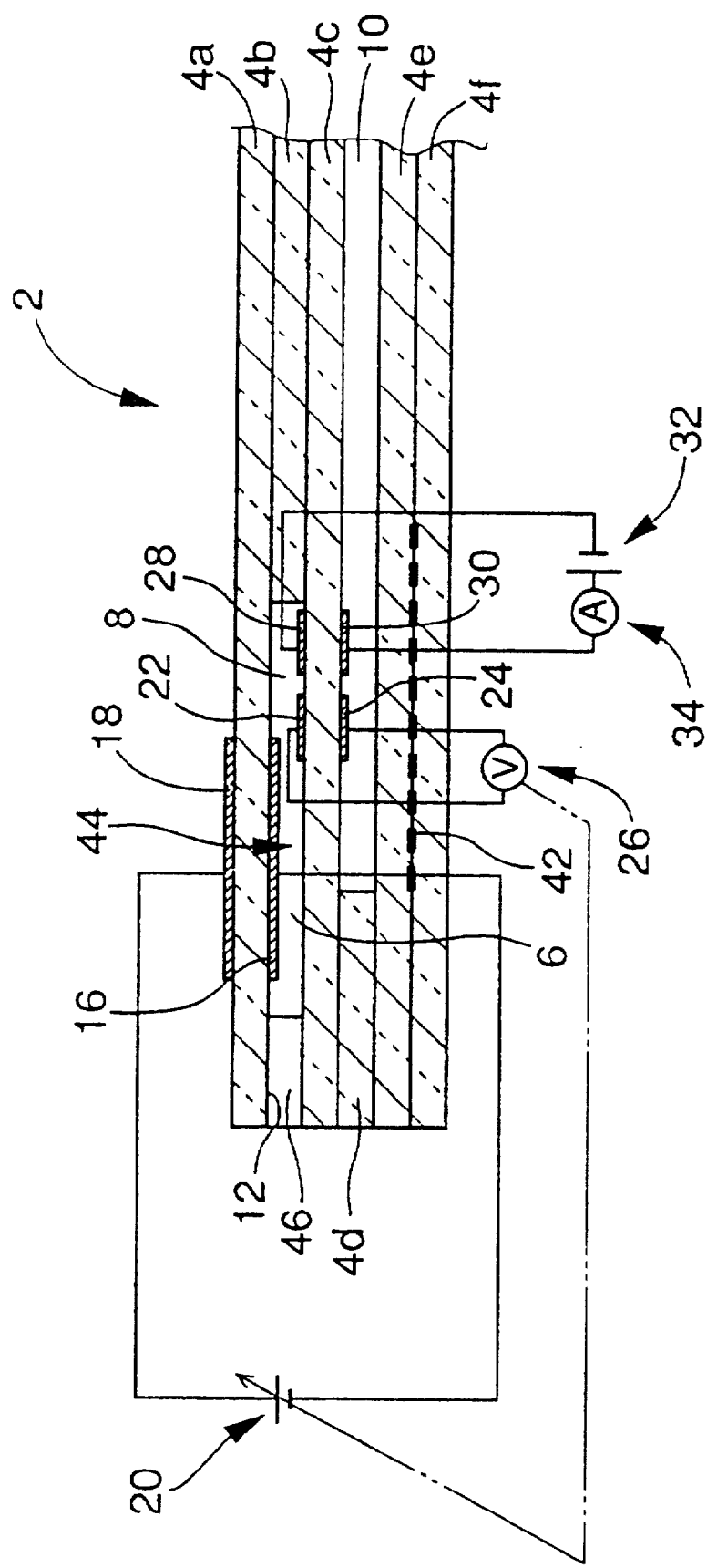
Figure 6:
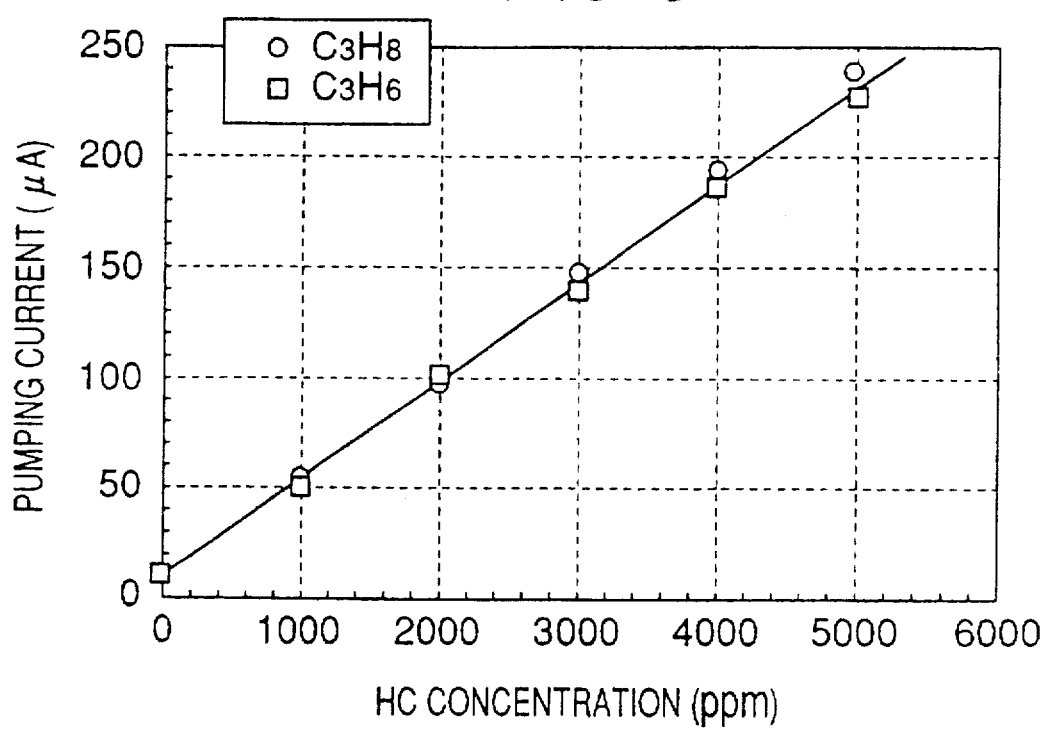
Figure 7:
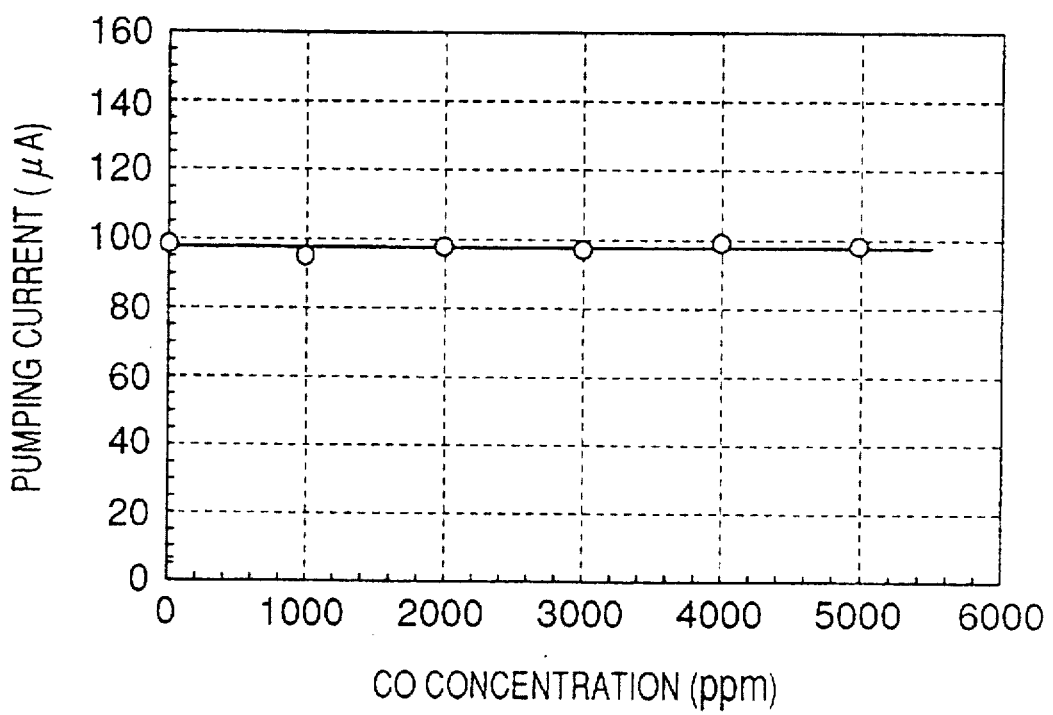
Figure 8:
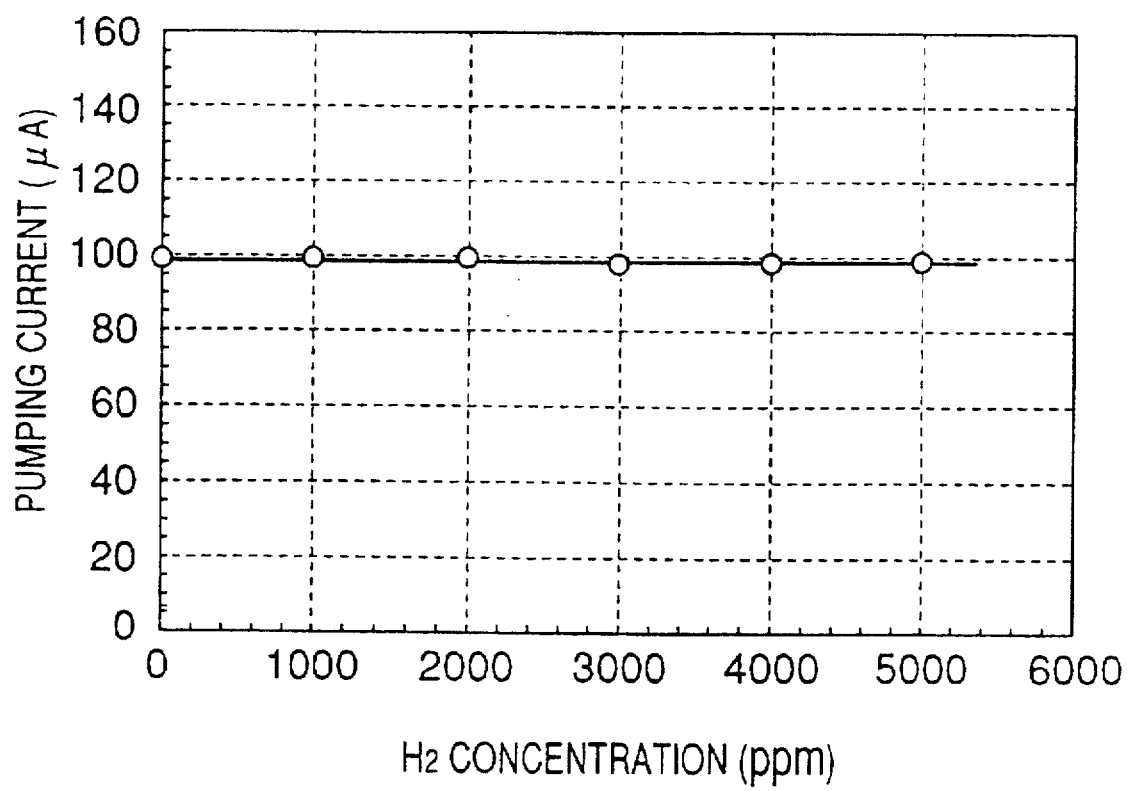
Figure 9:
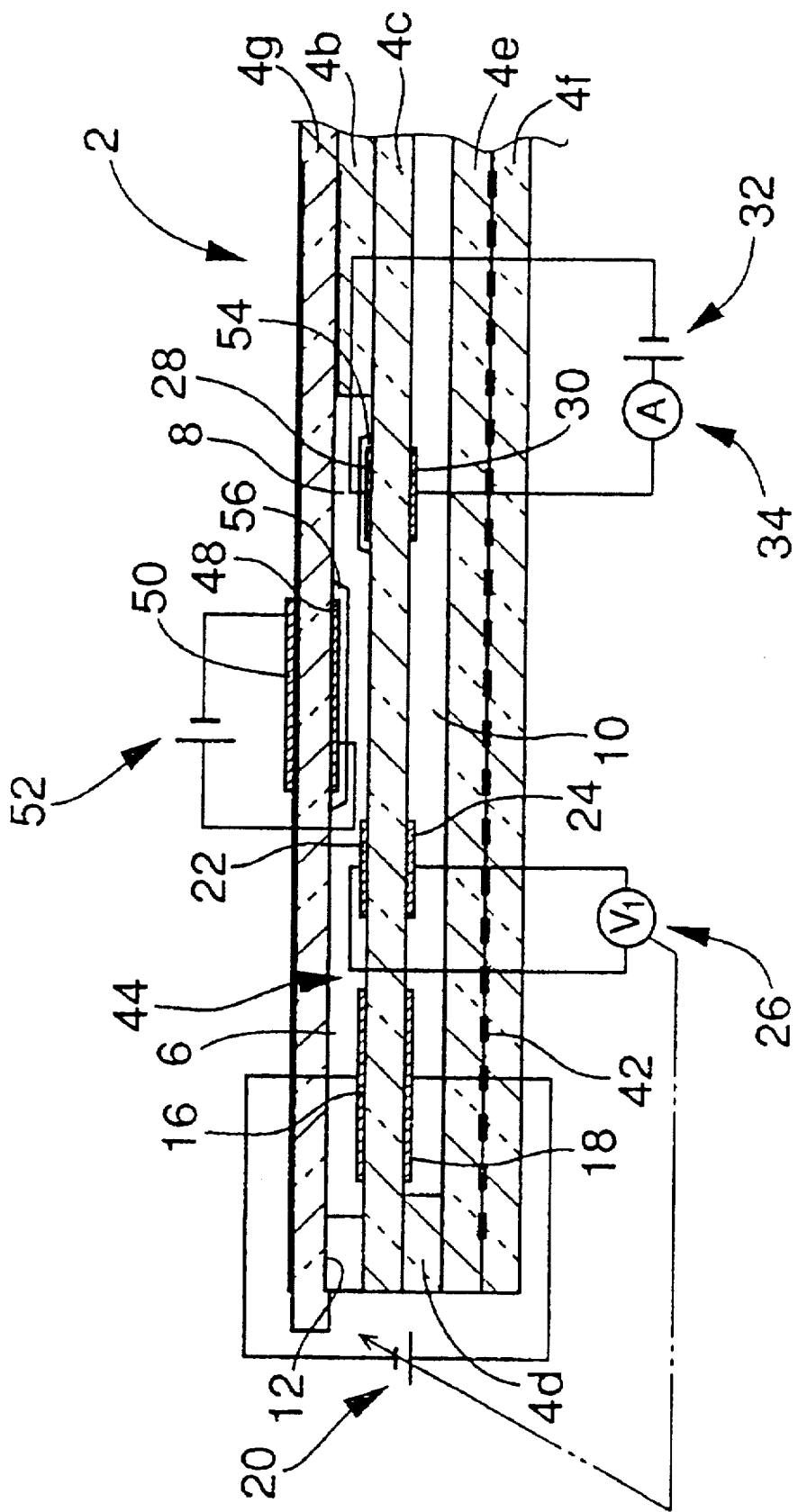
Figure 10:
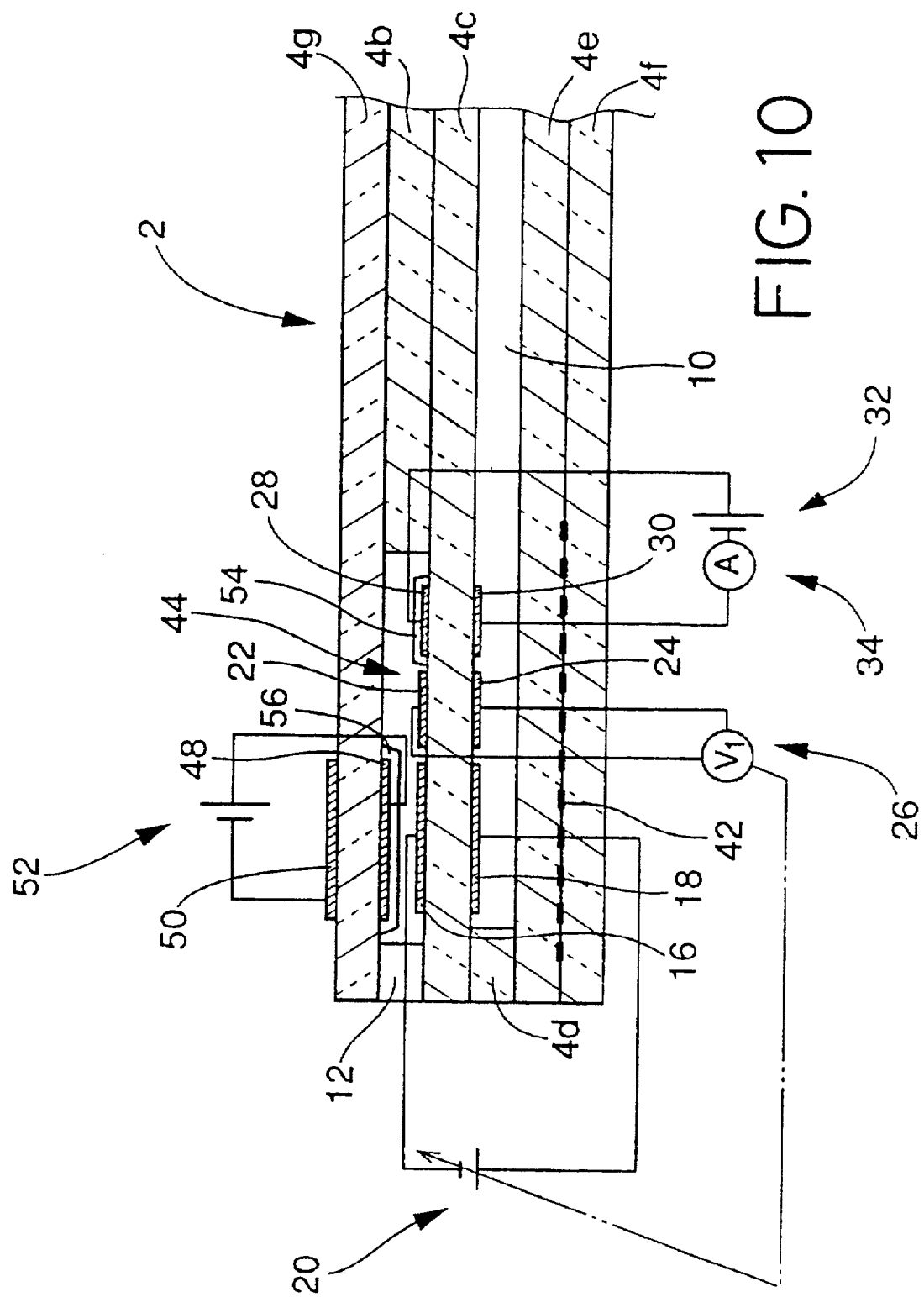
Figure 11:
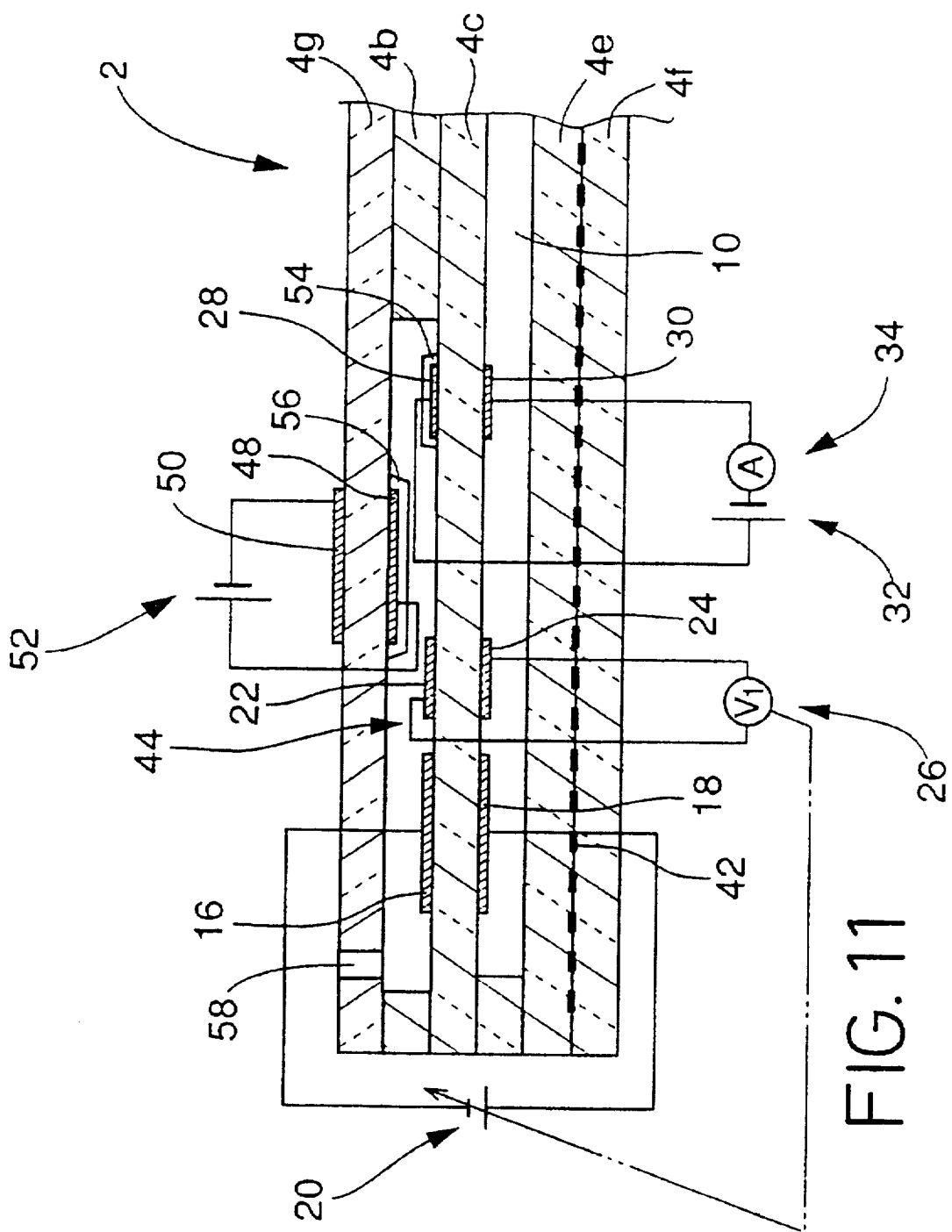
Figure 12:
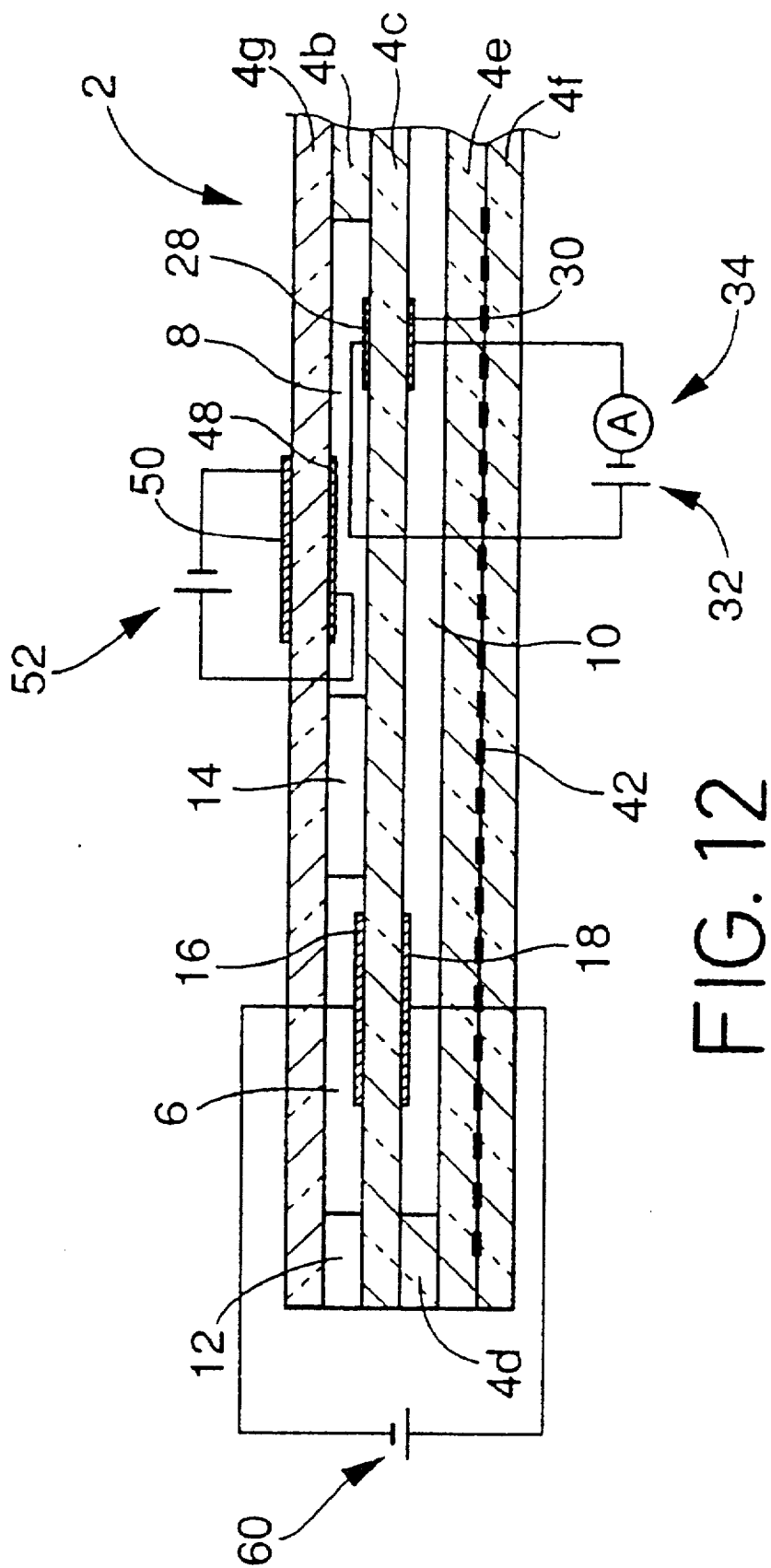
Figure 13:
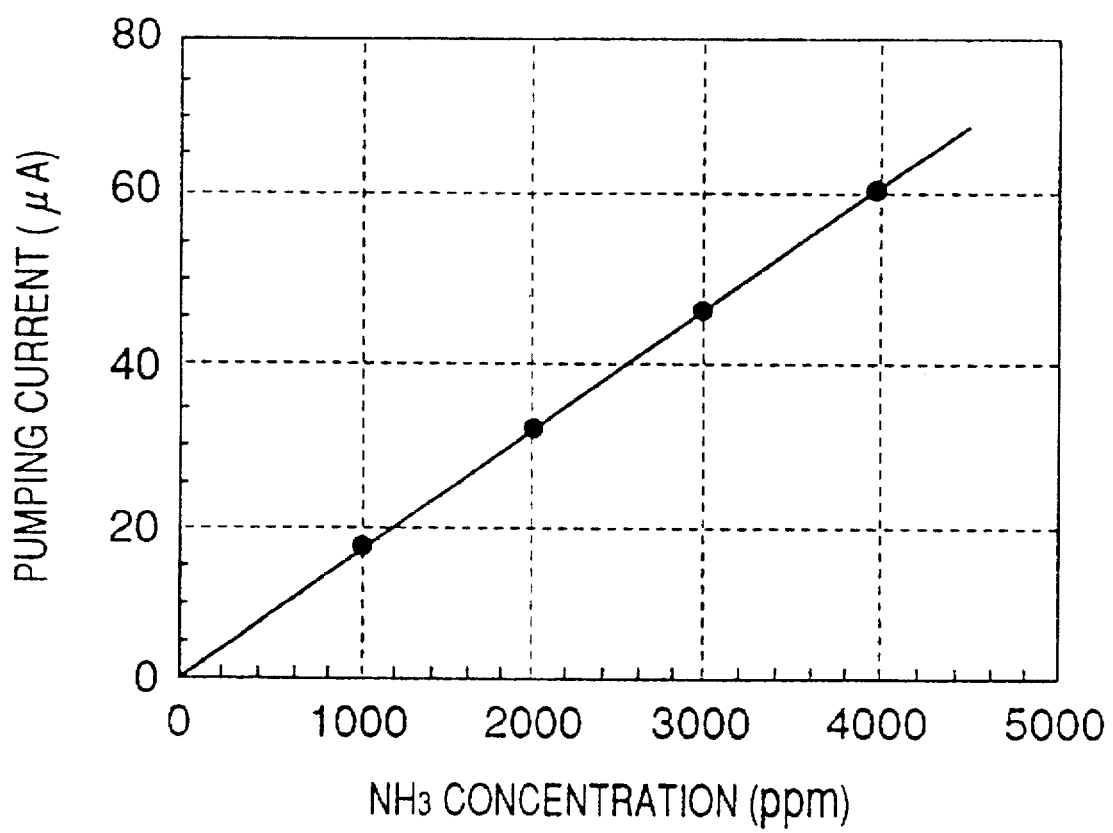

FIGS. 2(a) and 2(b) are views corresponding to those of FIGS. 1(a) and 1(b), showing a combustible gas component measuring apparatus according to a second embodiment of the present invention;

FIG. 3 is a graph indicating relationships between concentrations of combustible gas components and a pumping current of a second electrochemical oxygen pumping cell, which relationships were obtained by a sensing element shown in FIGS. 2(a) and 2(b);

FIG. 4 is a fragmentary enlarged view in cross section corresponding to that of FIG. 1(b), showing a sensing element used in a combustible gas component measuring apparatus according to a third embodiment of this invention;

FIGS. 5(a) and 5(b) are views corresponding to those of FIGS. 1(a) and 1(b), showing a sensing element used in a combustible gas component measuring apparatus according to a fourth embodiment of this invention;

FIG. 6 is a graph indicating a relationship between a HC concentration and a pumping current of a second electrochemical oxygen pumping cell, which relationship was obtained by the sensing element shown in FIGS. 5(a) and 5(b);

FIG. 7 is a graph indicating a relationship between a CO concentration and the pumping current of the second electrochemical oxygen pumping cell, which relationship was obtained by the sensing element of FIGS. 5(a) and 5(b);

FIG. 8 is a graph indicating a relationship between a $H_2$ concentration and the pumping current of the second electrochemical pumping cell, which relationship was obtained by the sensing element of FIGS. 5(a) and 5(b);

FIG. 9 is an enlarged view in cross section corresponding to that of FIG. 1(b), showing a sensing element used in a combustible gas component measuring apparatus according to a fifth embodiment of this invention;

FIG. 10 is an enlarged view in cross section corresponding to that of FIG. 1(b), showing a sensing element used in a combustible gas component measuring apparatus according to a sixth embodiment of the invention;

FIG. 11 is an enlarged view in cross section corresponding to that of FIG. 1(b), showing a sensing element used in a combustible gas component measuring apparatus according to a seventh embodiment of the invention;

FIG. 12 is an enlarged view in cross section corresponding to that of FIG. 1(b), showing a sensing element used in a combustible gas component measuring apparatus according to an eighth embodiment of the invention; and FIG. 13 is a graph indicating a relationship between a $NH_3$ concentration and a pumping current of a second electrochemical oxygen pumping cell, which relationship was obtained by the sensing element shown in FIGS. 1(a) and 1(b).

DETAILED DESCRIPTION OF THE PREFERRED EMBODIMENTS

Referring first to FIGS. 1(a) and 1(b), there is shown a typical example of a sensing element 2 used in an apparatus for measuring combustible gas components according to a first embodiment of this invention.

The sensing element 2 is a plate-like body having a relatively small width and a relatively large length. As is apparent from FIG. 1(b), the plate-like body of the sensing element 2 is an integral laminar structure including a plurality of dense, substantially gas-tight layers 4a, 4b, 4c, 4d, 4e and 4f of oxygen ion conductive solid electrolyte 4. These solid electrolyte layers 4a–4f are formed of zirconia ceramics or other known oxygen ion conductive solid electrolyte materials. This integral sensing element 2 is produced by co-firing a stack of unfired or green precursors of the oxygen ion conductive solid electrolyte layers 4a–4f, in a manner known in the art.

Within this integral sensing element 2, there are formed a first and a second internal cavity 6, 8, which are rectangular as seen in FIG. 1(a) and are planar as seen in FIG. 1(b). These first and second internal cavities 6, 8 are formed substantially gas-tightly with respect to the oxygen ion conductive solid electrolyte layers 4a–4f, and are spaced apart from each other in a direction of length of the sensing element 2, such that the first internal cavity 6 is located near one longitudinal end (distal end) of the sensing element 2. The first and second internal cavities 6, 8 provide a first and a second processing zone. The sensing element 2 also has a reference gas space in the form of a reference air passage 10 which is formed gas-tightly with respect to the first and second internal cavities 6, 8, the reference air passage 10 extends in the longitudinal direction of the sensing element 2, over a distance which covers the entire length of the second internal cavity 8 and a substantive portion of the length of the first internal cavity 6. The reference air passage 10 is open to the ambient atmosphere at the other longitudinal end (proximal end) of the sensing element 2.

The first and second internal cavities 6, 8 are defined by respective rectangular holes which are formed through the solid electrolyte layer 4b and which are closed by the adjacent upper and lower solid electrolyte layers 4a, 4c, so that the two cavities 6, 8 lie in substantially the same plane. Similarly, the reference air passage 10 is defined by a rectangular slot which is formed through the solid electrolyte layer 4d and which is closed by the adjacent upper and lower solid electrolyte layers 4c, 4e.

The solid electrolyte layer 4b has a slot which is closed by the adjacent upper and lower solid electrolyte layers 4a, 4c, so as to provide first diffusion control means in the form of a first diffusion control passage 12, which is open at the distal end portion of the sensing element 2. This first diffusion control passage 12 is formed in communication with the first internal cavity 6. In use, the sensing element 2 is positioned such that the distal end portion at which the first diffusion control passage 12 is open is exposed to an external subject gas space in which there exists a subject gas including combustible gas components, while the proximal end portion at which the reference air passage 10 is open is exposed to the ambient atmosphere, as indicated above. In operation of the sensing element 2, therefore, the subject gas to be measured is introduced into the first internal cavity 6 through the first diffusion control passage 12 under a predetermined diffusion resistance.

The solid electrolyte layer 4b has another slot formed between the two rectangular holes corresponding to the first and second internal cavities 6, 8. This slot is also closed by the upper and lower solid electrolyte layers 4a, 4c, whereby second diffusion control means in the form of a second diffusion control passage 14 is formed in communication with the first and second internal cavities 6, 8. The atmosphere in the first cavity 6 is introduced into the second cavity 8 through the second diffusion control passage 14 under a predetermined diffusion resistance.

A rectangular porous platinum (Pt) inner pumping electrode 16 is provided in contact with an area of the inner surface of the solid electrolyte layer 4a which is exposed to and partially defines the first internal cavity 6. Further, a rectangular porous platinum (Pt) outer pumping electrode 18 is provided in contact with an area of the outer surface of the solid electrolyte layer 4a which corresponds to the inner surface area on which the inner pumping electrode 16 is provided. These inner and outer pumping electrodes 16, 18 and the solid electrolyte layer 4a constitute a first electrochemical oxygen pumping cell. In operation of this pumping cell, a predetermined voltage is applied from an external variable-voltage power source 20, between the two pumping electrodes 16, 18 of the first electrochemical oxygen pumping cell, so as to cause a flow of an electric current in a direction from the outer pumping electrode 18 to the inner pumping electrode 16, so that oxygen in the atmosphere in the first internal cavity 6 is pumped into the external subject gas space. In the present sensing element 2, the porous platinum (Pt) pumping electrodes 16, 18 are formed of a cermet consisting of platinum (Pt) as an electrode metal and zirconia $ZrO_2$ as a ceramic material.

A rectangular porous platinum (Pt) measuring electrode 22 is provided in an area of one of the opposite surfaces of the solid electrolyte layer 4c which is exposed to the first cavity 6, while a rectangular porous platinum (Pt) reference electrode 24 is provided in contact with the corresponding area of the other surface of the solid electrolyte layer 4c which is exposed to the reference air passage 10. These measuring and reference electrodes 22, 24 and the solid electrolyte layer 4c constitute first oxygen partial pressure detecting means in the form of a first electrochemical sensing cell. As well known in the art, this first electrochemical sensing cell 4c, 22, 24 is adapted to detect the oxygen partial pressure of the atmosphere in the first cavity 6 on the basis of an output of a potentiometer 26 indicative of an electromotive force which is inducted between the measuring and reference electrodes 22, 24 according to a difference in oxygen concentration between the atmosphere within the first cavity 6 and the reference air (ambient atmosphere) within the reference air passage 10. The voltage of the variable-voltage power source is controlled based on the oxygen partial pressure of the atmosphere within the first cavity 6, which is detected by the potentiometer 26, so that the oxygen partial pressure within the first cavity 6 is maintained at a predetermined value.

A rectangular porous platinum (Pt) inner pumping electrode 28 is provided in contact with an area of one of the opposite surfaces of the solid electrolyte layer 4c which is exposed to the second internal cavity 8. Further, a rectangular porous platinum (Pt) outer pumping electrode 30 is provided in contact with the corresponding area of the other surface of the solid electrolyte layer 4c which is exposed to the reference air passage 10. These inner and outer pumping electrodes 28, 30 and the solid electrolyte layer 4c constitute a second electrochemical oxygen pumping cell. In operation, a predetermined voltage is applied from an external direct-current power source 32, between the inner and outer pumping electrodes 28, 30, so as to cause a flow of an electric current in a direction from the inner pumping electrode 28 to the outer pumping electrode 30, for pumping out oxygen from the reference air passage 10 into the second cavity 8, so that combustible gas components present in the atmosphere in the second cavity 8 can be oxidized and burned in contact with the oxygen thus introduced from the reference air passage 10 into the second cavity 8. The electric current flowing between the inner and outer pumping electrodes 28, 30, which is referred to as "pumping current", is measured by an ammeter 34.

A rectangular porous platinum (Pt) measuring electrode 36 is provided in another area of one of the opposite surfaces of the solid electrolyte layer 4c which is exposed to the second cavity 8, while a rectangular porous platinum (Pt) reference electrode 38 is provided in contact with the corresponding area of the other surface of the solid electrolyte layer 4c which is exposed to the reference air passage 10. These measuring and reference electrodes 36, 38 and the solid electrolyte layer 4c constitute second oxygen partial pressure detecting means in the form of a second electrochemical sensing cell. Like the first electrochemical sensing cell 4c, 22, 24, this second electrochemical sensing cell 4c, 36, 38 is adapted to detect the oxygen partial pressure of the atmosphere in the second cavity 8 on the basis of an output of a potentiometer 40 indicative of an electromotive force which is inducted between the measuring and reference electrodes 36, 38 according to a difference in oxygen concentration between the atmosphere within the second cavity 8 and the reference air within the reference air passage 10. The oxygen partial pressure in the second cavity 8 is detected by this second electrochemical sensing cell 4c, 36, 38 in order to assure that the amount of oxygen to be pumped out from the reference air passage 10 into the second cavity 8 by the second electrochemical oxygen pumping cell 4c, 28, 30 is substantially equal to or larger than an amount necessary to oxidize and burn the combustible gas components existing in the atmosphere within the second cavity 8. The voltage of the direct-current power source 32 is controlled based on the oxygen partial pressure of the atmosphere within the second cavity 8, which is detected by the potentiometer 40, so that the oxygen partial pressure (partial pressure of residual oxygen) within the second cavity 8 is maintained at a predetermined value.

Within the sensing element 2, there is embedded a heater 42 sandwiched by and between the adjacent upper and lower solid electrolyte layers 4e and 4f. This heater 42 is energized by a suitable external power source. For electrical insulation of the solid electrolyte layers 4e, 4f from the heater 42, thin electrically insulating layers are formed of alumina or other suitable ceramic material so as to cover the upper and lower surfaces of the heater 42. As shown in FIG. 1(b), the heater 42 has a length sufficient to cover the entire lengths of the first and second internal cavities 6, 8, so that the spaces within these cavities 6, 8 are heated to substantially equal temperatures, to thereby hold the first and second electrochemical oxygen pumping cells (4a, 16, 18, 4c, 28, 30) and the first and second electrochemical sensing cells (4c, 22, 24, 36, 38) at substantially the same elevated temperature.

As indicated above, the thus constructed sensing element 2 is positioned such that the distal end portion at which the first diffusion control passage 12 is open is exposed to the subject gas space in which the subject gas to be measured exists, while the proximal end portion at which the reference air passage 10 is open is exposed to the ambient atmosphere. Accordingly, the subject gas containing the combustible gas components is introduced in to the first cavity 6 through the first diffusion control passage 12 under the predetermined diffusion resistance. Where the subject gas is a combustion gas, this subject gas includes combustible gas components such as CO, $H_2$ and HC, as well as gas components such as $N_2$, $O_2$, $CO_2$ and $H_2O$. In operation of the sensing element 2, the first electrochemical oxygen pumping cell 4a, 16, 18 is operated to perform an oxygen pumping action by application of the predetermined voltage between the two pumping electrodes 16, 18, whereby oxygen is pumped out from the first internal cavity 6 into the external subject gas space so that the oxygen concentration or partial pressure of the atmosphere within the first cavity 6 is controlled to a predetermined level which is low enough to inhibit oxidization and burning or combustion of the combustible gas components within the first cavity 6.

For maintaining the oxygen concentration or partial pressure in the first cavity 6 at the predetermined low level as explained above, the electromotive force induced between the measuring and reference electrodes 22, 24 of the first electrochemical sensing cell is measured by the potentiometer 26, according to the Nernst equation well known in the art, and the voltage (supplied from the variable-voltage power source 20) between the two electrodes 16, 18 of the first electrochemical oxygen pumping cell is controlled to control the measured electromotive force to 930 mV at 700° C., for example. In this case, the oxygen partial pressure of the atmosphere within the first cavity 6 is controlled to about $10^{-20}$ atm. At this oxygen partial pressure, oxidization and burning or combustion of the combustible gas components such as HC, CO and $H_2$ is substantially impossible In essence, the voltage to be applied to the first electrochemical oxygen pumping cell 4a, 16, 18 is controlled so that the electromotive force between the pumping electrodes 16, 18 corresponds to a difference between the desired oxygen concentration in the first cavity 6 and the oxygen concentration of the reference air. The first diffusion control passage 12 functions to limit the rate of flow of the subject gas into the first cavity 6 during operation of the first electrochemical oxygen pumping cell, and thereby restrict the pumping current flowing through the first pumping cell.

As indicated above, the oxygen partial pressure within the first cavity 6 is maintained at a level low enough to inhibit the oxidization and burning or combustion of the combustible gas components in the atmosphere in the first cavity 6, in the presence of the inner and outer pumping electrodes 16, 18, even under heat due to a relatively high temperature of the external subject gas and due to heating by the heater 42. Generally, the oxygen partial pressure in the first cavity 6 is held at $10^{-14}$ atm or lower, preferably, $10^{-16}$ atm or lower. If the combustible gas components in the subject gas were oxidized and burned within the first cavity 6, it would not be possible to accurately measure the combustible gas components within the second cavity 8. In this sense, it is necessary to inhibit the oxidization and burning of the combustible gas components within the first cavity 6, in the presence of components (including at least a component of the inner pumping electrode 16) associated with the oxidization and burning of the combustible gas components. As a result of the oxygen pumping action performed by the first electrochemical oxygen pumping cell 4a, 16, 18, $O_2$ is removed from the atmosphere in the first cavity 6, and HC, CO and $H_2$ remain in the first cavity 6 as the combustible gas components.

The subject gas whose oxygen partial pressure has been controlled in the first cavity 6 is introduced into the second cavity 8 through the second diffusion control passage 14 under the predetermined diffusion resistances. The subject gas in the second cavity 8 is supplied with oxygen introduced from the reference air passage 10, by an oxygen pumping action performed by the second electrochemical oxygen pumping cell 4c, 28, 30 with the predetermined voltage being applied between the inner and outer pumping electrodes 28, 30 so as to cause a flow of the pumping current in the direction for pumping oxygen from the passage 10 into the second cavity 8. As a result, the oxygen partial pressure in the second cavity 8 is controlled so as to permit the oxidization and burning of the combustible gas components around the inner pumping electrode 28 which also functions as an oxidizing catalyst for the combustible gas components The pumping current flowing through this second electrochemical oxygen pumping cell corresponds to the amount of oxygen necessary for burning the combustible gas components. Therefore, the total concentration of the combustible gas components HC, CO and $H_2$ can be measured by measuring the pumping current. The total concentration of the combustible gas components in the second cavity 8 corresponds to the amount of diffusion of these components through the second diffusion control passage 14. Accordingly, the total concentration of the combustible gas components can be measured or determined on the basis of the measured total concentration within the second cavity 8.

Described in details the second electrochemical oxygen pumping cell is operated to pump oxygen from the reference air passage 10 into the second cavity 8, by an amount substantially equal to or larger than an an mount necessary for burning the combustion gas components. In other words, the second electrochemical oxygen pumping cell is operated so that the partial pressure of oxygen remaining in the second cavity 8 is held at a predetermined value. The amount of oxygen which is pumped into the second cavity 8 can be detected on the basis of the pumping current flowing through the pumping cell 4c, 28, 30. In this respect, it is noted that when the voltage applied between the pumping electrodes 28, 30 is held constant, the oxygen ion current flowing through the pumping cell corresponds to the predetermined value of the partial pressure of residual oxygen remaining after the burning of the combustible gas component. If the voltage applied between the pumping electrodes 28, 30 is held constant at 450 mV at 700° C., the pumping current flows through the pumping cell so that the residual oxygen partial pressure after the oxidization and burning of the combustible gas components in the second cavity 8 is held constant at $10^{-10}$ atm. In the present example of FIGS. 1(a) and 1(b), the voltage of the direct-current power source 32 for activating the second electrochemical oxygen pumping cell 4c, 28, 30 is controlled on the basis of the electromotive force detected by the second electrochemical sensing cell 4c, 36, 38, so that the voltage is held at a level necessary to hold the residual oxygen partial pressure at the predetermined constant value.

In the present sensing element 2, the oxygen ion conductive solid electrolyte body 4 may be formed of suitable known material other than zirconia ceramics. Further, the solid electrolyte layers 4a–4f and the various electrodes need not be co-fired. For instance, the electrodes may be formed by baking on the appropriate sintered solid electrolyte layers, and the individual sintered solid electrolyte layers some of which carry the electrodes are then bonded together with a suitable glass material.

The electrodes 16, 18, 22, 24, 28, 30, 36 and 38 are preferably formed of a porous cermet consisting of a mixture of an electrode metal (electrically conductive material) and a ceramic material, for improved adhesion or bonding to the solid electrolyte layers (ceramic substrates). However, these electrodes may consist solely of a metallic material of these electrodes, the inner pumping electrode 16 of the first electrochemical oxygen pumping cell and the measuring electrode 22 of the first electrochemical sensing cell are preferably formed of a material which has no or only a small degree of function as an oxidizing catalyst. To this end, it is desirable to use Au, Ni or similar electrode material for those electrodes 16, 22. In view of the firing temperature of the solid electrolyte material (e.g., zirconia) in the neighborhood of 1400° C., however, it is desirable to use an alloy of such electrode material (e.g., Au, Ni) and a suitable noble metal having a relatively high melting point such as Pt, Pd and Rh. Although such noble metals have a comparatively high function as the oxidizing catalyst, the function can be made sufficiently small if the alloys includes at least 1% of Au, Ni or similar electrode material. For instance, 1% by weight of Au is added to platinum (Pt), and zirconia ($ZrO_2$) is added to this alloy of the electrode materials such that volume ratio of (Pt and Au) to $ZrO_2$ is 60:40. In this instance, the functionality as the oxidizing catalyst of the obtained electrode may be sufficiently reduced.

On the other hand, the inner pumping electrode 28 of the second electrochemical oxygen pumping cell which is located within the second cavity 8 is preferably formed of a porous cermet using a noble metal such as Pt, Pd, Rh having a high degree of function as the oxidizing catalyst, since the combustible gas components in the cavity 8 need to be oxidized and burned by introduction of oxygen thereto by the oxygen pumping action of the second electrochemical oxygen pumping cell. In this case, the inner pumping electrode 28 can function also as an oxidizing catalyst layer for oxidizing the combustible gas components within the second cavity 8. However, the oxidizing catalyst layer may be provided in the second cavity 8 in addition to the inner pumping electrode 28. In this case, the oxidizing catalyst layer may be a porous ceramic body which carries a suitable known noble metal such as Pt, Pd, Rh as the oxidizing catalyst.

It is desirable that the voltage to be applied between the inner and outer pumping electrodes 28, 30 of the second electrochemical oxygen pumping cell for pumping oxygen from the reference air passage 10 into the second cavity 8 to oxidize and burn the combustible gas components in the atmosphere within the second cavity 8 be controlled so that the oxygen partial pressure in the second cavity 8 is as close as possible to the oxygen partial pressure of the atmosphere within the first cavity 6 (so that the pumping current of the second electrochemical oxygen pumping cell is as close as possible to zero when the concentration of the combustible gas components in the second cavity 8 is zero), in other words, it is desirable to control the voltage between the pumping electrodes 28, 30 so that the amount of oxygen to be pumped into the second cavity 8 is a minimum required for oxidizing and burning the combustible gas components in the atmosphere within the second cavity 8. Generally, the second electrochemical oxygen pumping cell is controlled to perform a pumping action so that the amount of oxygen to be pumped into the second cavity 8 by the second electrochemical oxygen pumping cell is almost equal to or larger than the amount necessary to burn the combustible gas components within the second cavity 8, and so that the residual oxygen partial pressure in the second cavity 8 is held constant Generally, it is desirable that the residual oxygen partial pressure is 1/1000 or lower of the total combustible gas components existing in the subject gas. If the residual oxygen partial pressure is higher than this level, the accuracy of measurement of the concentration of the combustible gas components tends to be lowered. To improve the measurement accuracy, it is preferred to maximize the oxygen partial pressure in the first cavity 6 while preventing the oxidization and burning or combustion of the combustible gas components within the first cavity 6. This is preferred because the oxygen partial pressure in the second cavity 8 can be more easily controlled to be close to that in the first cavity 6.

In the present sensing element 2, the predetermined voltage is applied from the direct-current power source 32 between the inner and outer pumping electrodes 28, 30 of the second electrochemical oxygen pumping cell, and the total concentration of the combustible gas components in the subject gas is determined on the basis of the output of the ammeter 34 indicative of the pumping current flowing through the oxygen pumping cell 4c, 28, 30. However, the concentration of the combustion gas components of the subject gas may be measured otherwise. For example, the measurement can be achieved by one of the following methods: providing a short-circuit in which the inner and outer pumping electrodes 30 are merely short-circuited and which does not includes the direct-current power source 32) and measuring a short-circuit current flowing through this short-circuit; providing a suitable resistor in such a short-circuit and measuring a short-circuit current flowing through the resistor; providing a short-circuit in which the inner and outer pumping electrodes 28, 30 are short-circuited via a suitable resistors and measuring a voltage across the pumping electrodes; and short-circuiting the pumping electrodes 28, 30 with a predetermined current, and measuring a voltage across these electrodes Referring next to FIGS. 2(a) and 2(b) corresponding to those of FIGS. 1(a) and 1(b), there will be described a combustible gas component measuring apparatus constructed according to a second embodiment of the present invention Unlike the sensing element 2 shown in FIGS. 1(a) and 1(b), the sensing element 2 of the apparatus shown in FIGS. 2(a) and 2(b) is characterized by a single relatively large internal space 44, which has a generally elongate rectangular shape as seen in FIG. 2(a), and which is planar as seen in FIG. 2(b). This internal space 44 is in communication with the external subject gas space through the first diffusion control passage 12. The internal space 44 has a first processing zone in the form of a first cavity portion 6 (hereinafter referred to as "first cavity 6") adjacent to the first diffusion control passage 12, and a second processing zone in the form of a second cavity portion 8 (hereinafter referred to as "second cavity 8") adjacent to the first cavity 6. The atmosphere flows from the first cavity 6 into the second cavity 8 under a predetermined diffusion resistance Within these first and second cavities 6, 8, there are provided the inner pumping electrode 16 of the first electrochemical oxygen pumping cell, the measuring electrode 22 of the first electrochemical sensing cell, and the inner pumping electrode 28 of the second electrochemical oxygen pumping cell.

The sensing element 2 of the present second embodiment is also characterized by the second electrochemical oxygen pumping cell 4c, 28, 30 provided for the second cavity 8 which is the inner portion of the internal space 44 remote from the first diffusion control passage 12. Described more specifically, the direct-current power source 32 is a constant-voltage power source adapted to apply a constant voltage between the inner and outer pumping electrodes 28, 30, for the second electrochemical oxygen pumping cell 4c, 28, 30 to perform an intended oxygen pumping action. The voltage of the constant-voltage power source 32 is determined in view of the oxygen concentration of the atmosphere within the first cavity 6, so that the pumping current flowing through the pumping cell 4c, 28, 30 establishes a predetermined partial pressure of the residual oxygen remaining after the burning or combustion of the combustible gas components within the second cavity 8. The pumping current is detected by the ammeter 34. The present embodiment wherein the direct-current power source 32 is a constant-voltage power source does not require second oxygen partial pressure detecting means (second electrochemical sensing cell) as required in the first embodiment The other portions of the sensing element 2 of this second embodiment are identical with the corresponding portions of the first embodiment which have been described above in detail.

For example, the sensing element 2 according to the present second embodiment has a width of 4.2 mm, a length of 64 mm and a thickness of 1.4 mm. To produce the sensing element 2, green tapes corresponding to the solid electrolyte layers 4a–4f are formed using zirconia as a suitable oxygen ion conductive solid electrolyte material. The appropriate green tapes are subjected to punching operations to form slots and a hole which are precursors of the first diffusion control passage 12, internal space 44 and reference air passage 10. Then, the electrodes 16, 18, 22, 24, 28, 30 are formed by printing on the appropriate green tapes. In the present embodiment, the electrodes are formed of a porous cermet of Pt and $ZrO_2$. The volume ratio of Pt to $Al_2O_3$ is 60:40. The heater 42 is formed of a cermet conductor of Pt and $ZrO_2$ whose volume ratio is 90:10. The upper and lower surfaces of the heater 42 are covered by films of alumina ($Al_2O_3$) having a thickness of about 20 µm, which are formed by printing, for electrically insulating the zirconia solid electrolyte 4 from the heater 42. The heater 42 has a resistance (e.g., 7 Ω) determined to maintain the temperature in the internal space 44 at a desired temperature (e.g., 600° C.) during energization of the heater 42 with a nominal voltage of 12 V. The green tapes corresponding to the solenoid electrolyte layers 4a–4f, which have thus been subjected to the punching and printing operations, are laminated under heat and pressure, and co-fired at 1400° C. so as to provide the desired sensing element 2.

In operation of the sensing element 2 of FIGS. 2(a) and 2(b) to measure the concentration of the combustible gas components in the subject gas, the subject gas is introduced into the internal space 44 through the first diffusion control passage 12 while the temperature in the space 44 is maintained at 600° C. by energization of the heater 42. The voltage of the variable-voltage power source 20 to be applied between the measuring and reference electrodes 22, 24 is feedback-controlled so as to be held at 900 mV. As a result, oxygen in the first cavity is pumped into the external subject gas space by the first electrochemical oxygen pumping cell 4a, 16, 18, whereby the oxygen partial pressure (concentration) of the atmosphere within the first cavity 6 is held at about $10^{-23}$ atm. Under such temperature and oxygen partial pressure conditions, the oxidization of the combustible gas components HC, CO and $H_2$ in the subject gas in the first cavity 6 will not take place.

The atmosphere (including the combustible gas components CO, $H_2$ and HC) in the first cavity 6, whose oxygen concentration has been controlled to be substantially zero, diffuses toward the inner portion of the internal space 44 and reaches the second cavity 8, contacting the inner pumping electrode 28. At this time, the oxygen partial pressure of the atmosphere in the second cavity 8 is close to zero, and the atmosphere in the reference air passage 10 in which the outer pumping electrode 30 is disposed is the ambient atmosphere, so that the electromotive force induced between the inner and outer pumping electrodes 28, 30 is in the neighborhood of 1 V, more precisely, about 900 mV. Consequently, a constant voltage of 455 mV of the direct-current power source 32 is applied between the inner and outer pumping electrodes 28, 30 of the second electrochemical oxygen pumping cell, so as to cause a flow of a pumping current in a direction from the inner pumping electrode 28 as the positive electrode toward the outer pumping electrode 30.

The voltage of the direct-current power source 32 is determined to be a sum of a voltage Vs (=450 mV) corresponding to the predetermined or desired residual oxygen partial pressure in the atmosphere in the second cavity 8, and a voltage drop Vd (5 mV) due to the pumping current and a pump impedance of the second electrochemical oxygen pumping cell. Namely, the voltage of the power source 32 is determined to be (Vs+Vd)=455 mV. The voltage drop Vd, which varies with the pumping current, is a few or several mV at the most, and may be ignored, since the pumping current is on the order of μA and the pump impedance is about 100 Ω.

As a result of the oxygen pumping action of the second electrochemical oxygen pumping cell energized with the predetermined voltage of 455 mV supplied from the constant-voltage direct-current power source 32, oxygen is pumped from the reference air in the reference air passage 10 into the atmosphere in the second cavity 8, whereby the combustible gas components in the atmosphere in the second cavity 8 are oxidized and burned. The partial pressure of the residual oxygen remaining in the second cavity 8 after the burning of the combustible gas components is about $10^{-12}$ atm at 600° C. where the energization voltage of the second electrochemical oxygen pumping cell is 450 mV. In other words, the voltage supplied from the power source 32 to the pumping cell is determined so that the residual oxygen partial pressure in the second cavity 8 is equal to $10^{-12}$ atm. The pumping current of the pumping cell is measured by the ammeter 34. The amount of oxygen necessary for burning the combustible gas components in the second cavity 8, that is, the pumping current induced by the direct-current power source 32 is proportional to the concentration of the combustible gas components in the atmosphere within the second cavity 8. Therefore, the concentration of the combustible gas components in the subject gas can be determined by measuring the pumping current.

The graph of FIG. 3 indicates changes of the pumping current between the inner and outer pumping electrodes 28, 30 of the second electrochemical oxygen pumping cell, in relation to the concentration of a combustible gas component $C_3H_8$ (hydrocarbon), CO or $H_2$ included in specimen gas (including $N_2$ as carrier gas, and 7% of $H_2O$), when the pumping current was measured in the apparatus provided with the sensing element 2 as shown in FIGS. 1 and 2, by changing the concentration of each combustible gas component from 0 to 5000 ppm in increments of 1000 ppm. Namely, the graph shows the relationships between the measured pumping current and the actual concentrations of the combustible gas components included in the specimen gases.

It will be understood from the graph of FIG. 3 that the detecting sensitivity (pumping current/combustible gas concentration) of the sensing element 2 with respect to $C_3H_8$ as one of the hydrocarbon (HC) combustibles was as high as about 10 times that with respect to the other combustibles CO and $H_2$. This shows that the present sensing element 2 is particularly effective to measure the hydrocarbon combustibles with high accuracy. Generally, combustion gases such as automobile combustion gases have a considerably large number of hydrocarbon (HC) combustibles whose number of carbon atoms is larger than that of $C_3H_8$ in the example of FIG. 3. In the light of this fact, the sensing element 2 is practically more sensitive to the hydrocarbons included in combustion gases that are actually produced in various industries.

Referring to FIG. 4, there is shown a sensing element of a combustible gas component measuring apparatus according to a third embodiment of this invention, which is different from the sensing element 2 of FIGS. 2(a) and 2(b), in connection with the first diffusion control passage 12 and heater 42.

In the sensing element 2 of FIG. 4 according to the third embodiment, the first diffusion control passage 12 is filled with a selective oxidizing catalyst 46 which is a porous alumina containing cerium oxide ($CeO_2$). The external subject gas is introduced into the internal space 44 through the selective oxidizing catalyst 46. The selective oxidizing catalyst 46 has a function of selectively oxidizing and burning $H_2$ and CO, which are included as the combustible gas components in the subject gas. That is, the selective oxidizing catalyst 46 has substantially no catalytic function of oxidizing the hydrocarbon (HC) combustibles included in the subject gas. Further, the heater 42 provided in the present embodiment of FIG. 4 is located so as to effectively heat only the inner portion or second cavity 8 of the internal space 44, and does not extend to cover the selective oxidizing catalyst 46, so that the oxidizing catalyst 46 provided near the distal end of the sensing element 2 remote from the space 44 is held at a relatively low temperature For instances the heater 42 in the present embodiment is designed and located so that the selective oxidizing catalyst 46 is held at 350° C. while the inner pumping electrode 28 is held at 600° C. Under this temperature distribution, the selective oxidizing catalyst 46 is placed in a better condition for selective oxidization of the combustible gas components, that is, the catalyst 46 is more likely to burn CO and $H_2$ and less likely to burn HC. For selective oxidization of CO and $H_2$, the upper limit of the temperature of the catalyst 46 is generally 600° C., preferably, 500° C.

In the sensing element 2 of the third embodiment in which the selective oxidizing catalyst 46 is disposed upstream of the first cavity 6 as seen in the direction of flow of the subject gas from the external subject gas space into the first cavity 6, HC and CO included in the subject gas are selectively oxidized during introduction of the subject gas through the selective oxidizing catalyst 46. Generally, CO and $H_2$ are more combustible than HC, and there is a large difference in combustibility between CO, $H_2$ and HC at a temperature of about 300–500° C. Since the temperature of the first diffusion control passage 12 during energization of the heater 42 is about 350° C., the selective oxidizing catalyst 46 provided in the diffusion control passage 12 is more likely to burn CO and $H_2$ and less likely to burn HC. Further, the porous alumina containing $CeO_2$ used for the selective oxidizing catalyst 46 enables the catalyst 46 to have a high catalytic function of selectively oxidizing CO and $H_2$. In particular, $CeO_2$ has a comparatively high efficiency of oxidization of CO and $H_2$, and a comparatively low efficiency of oxidization of HC. The temperature of the catalyst 46 and the use of $CeO_2$ for the catalyst 46 have a synergistic effect to efficiently remove CO and $H_2$ from the subject gas while minimizing the oxidization of HC, before the subject gas is introduced into the internal space 44. In this space 44, the oxygen partial pressure of the introduced subject gas is first controlled by an oxygen pumping action of the first electrochemical oxygen pumping cell, to a predetermined low level at which hydrocarbons (HC) as combustible gas components cannot be substantially burned Then, the hydrocarbons are oxidized and burned in the inner portion of the space 44, namely, in the second cavity 8, in the presence of oxygen introduced therein by an oxygen pumping action of the second electrochemical oxygen pumping cell The concentration of the hydrocarbons in the subject gas can be selectively determined by measuring or determining the amount of oxygen necessary for burning the hydrocarbons, that is, by measuring the pumping current between the inner and outer pumping electrodes 28, 30 of the second electrochemical oxygen pumping cell.

As explained above, it is desirable to use porous alumina containing $CeO_2$ as the selective oxidizing catalyst 46 for selectively oxidizing CO and $H_2$ of the combustible gas components in the subject gas, since it exhibits a high catalytic function to oxidize CO and $H_2$ and a low catalytic function to oxidize HC, and also functions as a catalyst for converting aqueous gases. However, other materials may be used as the selective oxidizing catalyst 46. For example, it is possible to use a porous body containing Au or $SnO_2$ in place of $CeO_2$, which is highly capable of selectively oxidizing CO and $H_2$. Since porous ceramics generally have a catalytic function for oxidization, the selective oxidizing catalyst 46 may be formed of a porous body consisting solely of a ceramic material such as alumina. It is also noted that the sensing element 2 may be designed or conditioned to relatively easily oxidize CO and $H_2$ while inhibiting the oxidization of HC, without using the selective oxidizing catalyst 46. This condition may be established by suitably selecting the material of the inner pumping electrode 16 in the internal space 44, and the oxygen partial pressure and temperature of the sensing element 2. While the catalyst 46 fills the entirety of the first diffusion control passage 12 in the embodiment of FIG. 4, the position and size of the catalyst 46 may be suitably selected. For instance, the catalyst 46 may be disposed at an inlet portion of the first diffusion control passage 12 adjacent to the distal end face of the sensing element 2. A selective oxidizing catalyst capable of oxidizing and burning CO and $H_2$ may be disposed within the internal space 44, provided the catalyst will not burn a desired combustible gas component (e.g., HC) to be measured.

Referring next to FIGS. 5(a) and 5(b) corresponding to FIGS. 1(a) and 1(b), there are shown a sensing element of a combustible gas component measuring apparatus constructed according to a fifth embodiment of this invention.

Unlike the sensing elements 2 described above, the sensing element 2 of FIGS. 5(a) and 5(b) includes a proton ion conductive solid electrolyte layer 4g in place of the oxygen ion conductive solid electrolyte layer 4a. The proton ion conductive solid electrolyte layer 4g consists of $SrCeO_3$, and is superposed on the oxygen ion conductive solid electrolyte layers 4b–4f, to form the integral sensing element 2. An inner proton pumping electrode 48 is provided on an area of an inner surface of the proton ion conductive solid electrolyte layer 4g which is exposed to and partially defines the second cavity 8. On the corresponding area of the outer surface of the proton ion conductive solid electrolyte layer 4g, there is provided an outer proton pumping electrode 50 in aligned relationship with the inner proton pumping electrode 48. These two proton pumping electrodes 48, 50 are connected to a proton pumping power source (direct current) 52, so that proton ($H_2$) existing in the atmosphere within the second cavity 8 is pumped out into the subject gas space. In the present embodiment, the proton ion conductive solid electrolyte layer 4g and the inner and outer proton pumping electrodes 48, 50 constitute a proton pump. In the present sensing element 2, all electrodes 18, 22, 24, 28, 30, 48, 50 except the inner pumping electrode 16 of the first electrochemical oxygen pumping cell are formed of the same material. Described more specifically, the inner pumping electrode 16 is formed of a porous cermet consisting of a Pt—Au alloy (including 1% by weight of Au) and $ZrO_2$, wherein the volume ratio of (Pt and Au) to $ZrO_2$ is 60:40. The other electrodes 18, 22, 24, 28, 30 including the two proton pumping electrodes 48, 50 are all formed of a porous cermet consisting of Pt and $ZrO_2$ wherein the volume ratio of Pt to $ZrO_2$ is 60:40, as in the second embodiment of FIGS. 2(a) and 2(b). Further, the inner and outer pumping electrodes 16, 18 of the first electrochemical oxygen pumping cell are provided on the opposite surfaces of the oxygen ion conductive solid electrolyte layer 4c such that the outer pumping electrode 18 is exposed to the reference air passage 10. Thus, the first electrochemical oxygen pumping cell is constituted by the solid electrolyte layer 4c and the two pumping electrodes 16, 18.

In operation of the sensing element 2 of the present fourth embodiment of FIGS. 5(a) and 5(b), the heater 42 is energized to maintain the temperature of the sensing element 2 at 700° C. Under this heating condition, the subject gas is introduced in to the first cavity 6 through the first diffusion control passage 12. The voltage of the variable-voltage power source 20 is feedback-controlled so that the voltage between the measuring and reference electrodes 22, 24 of the first electrochemical sensing cell (first oxygen partial pressure detecting means) is held constant at 880 mV. Accordingly, the oxygen pumping action of the first electrochemical oxygen pumping cell 4c, 16, 18 is controlled so that oxygen in the subject gas introduced into the first cavity 6 is pumped into the reference air passage 10, whereby the oxygen concentration or partial pressure of the atmosphere within the first cavity 6 is held at a predetermined low level, about $10^{-19}$ atm in this example, at which the combustible gas components cannot be substantially burned. In such temperature and oxygen partial pressure condition, oxidization of HC, CO and $H_2$ is unlikely to occur in the first cavity 6, and these combustible gas components remain in the atmosphere within the first cavity 6.

The atmosphere whose oxygen partial pressure has been controlled to the predetermined level in the first cavity 6 without oxidization of the combustible gas components is introduced into the second cavity 8 through the second diffusion control passage 14. In the second cavity 8, the atmosphere is initially subjected to a proton pumping action of the proton pump 4g, 48, 50, so that proton ($H_2$) in the atmosphere is pumped out of the second cavity 8. In operation of the proton pump, a voltage of 900 mV is applied from the proton pumping power source 52 between the two electrodes 48, 50. As a result of pumping of $H_2$ by the proton pump 4g, 48, 50, the amount of $H_2$ in the right member of a reaction formula $CO+H_2O \rightleftharpoons CO_2+H_2$ is reduced toward zero, and the chemical equilibrium is lost, whereby the reaction progresses in the right direction as seen in the formula. Further, $H_2$ produced by the reaction is also immediately pumped out by the proton pumping action of the proton pump, so that the rightward reaction in the above formula is continued. The proton pump exhibits a current-limiting characteristic at the pumping current larger than a value corresponding to the amount of CO which diffuses into the second cavity 8 through the second diffusion control passage 14, so that the partial pressure of $H_2$, namely, the partial pressure of CO within the second cavity 8 is made close to zero.

Thus, the oxygen partial pressure of the atmosphere is first substantially zeroed in the first cavity 6, and then the concentrations of CO and $H_2$ in the atmosphere are then substantially zeroed in a portion of the second cavity 8 corresponding to the proton pump 4g, 48, 50, but with HC still remaining as the combustible gas components. The atmosphere is then directed to a portion of the second cavity 8 corresponding to the second electrochemical oxygen pumping cell 4c, 28, 30. Since the oxygen partial pressure around the inner pumping electrode 28 is substantially zero while the atmosphere in the reference air passage 10 is the ambient atmosphere, the electromotive force inducted between the inner and outer pumping electrodes 28, 30 is almost equal to 1 V (about 880 mV). In this condition, therefore, a predetermined voltage (455 mV in this example) of the direct-current power source 32 is applied between the inner and outer pumping electrodes 28, 30, so as to cause a flow of pumping current in a direction from the inner pumping electrode 28 toward the outer pumping electrode 30. The voltage of the power source 32 is determined to be a sum of a voltage Vs (=450 mV) corresponding to the predetermined or desired residual oxygen partial pressure in the atmosphere in the second cavity 8, and a voltage drop Vd (5 mV) due to the pumping current and a pump impedance of the second electrochemical oxygen pumping cell. Namely, the voltage of the power source 32 is determined to be (Vs+Vd)=455 mV. The voltage drop Vd, which varies with the pumping current, is a few or several mV at the most, and may be ignored, since the pumping current is on the order of μA and the pump impedance is about 50 Ω.

As a result of the oxygen pumping action of the second electrochemical oxygen pumping cell energized with the predetermined voltage of 455 mV supplied from the constant-voltage direct-current power source 32, oxygen is pumped from the reference air in the reference air passage 10 into the atmosphere in the second cavity 8, whereby the combustible gas components (HC) in the atmosphere in the second cavity 8 react with the introduced oxygen and are oxidized. The partial pressure of the residual oxygen remaining in the second cavity 8 after the oxidizing reaction is about $10^{-10}$ atm. In other words, the pumping current flows through the second electrochemical oxygen pumping cell 4c, 28, 30 so that the residual oxygen partial pressure in the second cavity 8 is equal to $10^{-10}$ atm. This pumping current is measured by the ammeter 34. The amount of oxygen necessary for burning HC as the combustible gas components in the second cavity 8, that is, the pumping current induced by the direct-current power source 32 is proportional to the HC concentration of the atmosphere within the second cavity 8. Therefore, the HC concentration of the subject gas can be determined by measuring the pumping current.

The graph of FIG. 6 indicates a change of the pumping current between the inner and outer pumping electrodes 28, 30 of the second electrochemical oxygen pumping cell, in relation to the HC concentration of specimen gas, when the pumping current was measured by an apparatus including the sensing element 2 of FIGS. 5(a) and 5(b), by changing the HC concentration from 0 to 5000 ppm in increments of 1000 ppm. Namely, the graph shows the relationships between the pumping current measured by the ammeter 34 and the actual concentration of HC included in the specimen gases. Each specimen gas used included $N_2$ as a carrier gas, had $H_2$ concentration of 5%, and included $C_3H_8$ or $C_3H_6$ as hydrocarbon It will be understood from the graph of FIG. 6 that the pumping current values measured for the specimen gases including $C_3H_8$ are slightly higher than those for the specimen gases including $C_3H_6$. That is, it appears that the detecting sensitivity of the sensing element 2 with respect to $C_3H_8$ was slightly higher than the sensitivity with respect to $C_3H_6$. This is supposed to be attributable to decomposition of $C_3H_8 \rightarrow C_3H_6+H_2$, which is considered to take place simultaneously with the pumping of $H_2$. It is also noted that the decomposition of hydrocarbon $C_nH_{2n}$ is relatively difficult. This difficulty may be considered to cause the sensing element 2 to have substantially similar detecting sensitivity to $C_3H_8$ and $C_3H_6$. Thus, it is found that the sensitivity of the sensing element 2 is generally proportional to the number of carbon atoms of HC. The graph of FIG. 6 indicates the pumping current of about 10 μA when the HC concentration is 0 ppm. This pumping current corresponds to the concentration of the residual $H_2$ and CO, and is always constant, having no influence on the measurement of the HC concentration by the sensing element 2.

The graphs of FIGS. 7 and 8 indicate changes of the pumping current in relation to the CO and $H_2$ concentrations of specimen gas. The specimen gas included $N_2$ as a carrier gas, $H_2O$ concentration of 5%, and 2000 ppm of $C_3H_8$. The pumping current was measured by changing the concentration of CO or $H_2$ as an interfering gas from 0 to 5000 ppm in increments of 1000 ppm. The relationship between the measured pumping current and the CO concentration was indicated in the graph of FIG. 7, and the relationship between the measured pumping current and the $H_2$ concentration is indicated in the graph of FIG. 8.

It will be understood from the graphs of FIGS. 7 and 8 that the combustible gas components CO and $H_2$ included in the subject gas together with HC will not have an influence on the output of the sensing element 2 as representing the HC concentration.

Thus, the sensing element 2 according to the fourth embodiment of FIGS. 5(a) and 5(b) is capable of accurately detecting the HC concentration of the subject gas, without an influence of the other combustible gas components, on the basis of the amount of oxygen necessary to burn the hydrocarbon (HC).

Referring to FIG. 9 corresponding to FIG. 5(b), there is shown a sensing element of a combustible gas component measuring apparatus according to a fifth embodiment of this invention. Unlike the sensing element 2 of the fourth embodiment of FIGS. 5, the sensing element of this fifth embodiment includes a diffusion control layer 54 consisting of porous alumina, which constitutes a major part of second diffusion control means. This diffusion control layer 54 is formed so as to cover the inner pumping electrode 28 of the second electrochemical oxygen pumping cell. The sensing element of FIG. 8 also includes an aqueous gas converting catalyst layer 56 consisting of $Cr_2O_3$—$Fe_3O_4$. This aqueous gas converting catalyst layer 56 is formed so as to cover the inner proton pumping electrode 48 of the proton pump 4g, 48, 50.

In the sensing element 2 of this fifth embodiment, the aqueous gas converting catalyst layer 56 formed on the inner proton pumping electrode 48 promotes or facilitates conversion of Co in the atmosphere in the second cavity 8 to $H_2$, and is therefore effective to remove CO from the atmosphere. Thus, the provision of the catalyst layer 58 permits reduction of the residual CO concentration of the atmosphere, so that the pumping current when the HC concentration is zero can be made close to zero. In addition, the diffusion control layer 54 of porous alumina formed by printing on the inner pumping electrode 28 provides a major portion of the second diffusion control means. The sensing element 2 employing this second diffusion control means is simpler in construction. Further, the alumina of the diffusion control layer 54 is effective to burn HC in the atmosphere, contributing to an improvement in the accuracy of measurement of the sensing element 2. The present sensing element 2 is capable of burning HC while the oxygen concentration of the atmosphere in the second cavity 8 (portion of the inner space 44 remote from the distal end of the sensing element 2) is held relatively low. Accordingly, the amount of oxygen which diffuses from the second cavity 8 into the first cavity 6 is reduced, and the stability of the oxygen concentration of the atmosphere in the first cavity 6 is advantageously improved. Further, the present arrangement makes it possible to reduce the dimensions of the internal space 44 and the surface area to be heated by the heater 42, leading to reduced power consumption by the heater 42.

There will be described sixth and seventh embodiments of this invention by reference to FIGS. 10 and 11. Unlike the fifth embodiment of FIG. 9, the sixth embodiment shown in FIG. 10 is characterized in that the proton pump 4g, 48, 50 is located at one end of the internal space 44 adjacent to the first diffusion control passage 12. This arrangement not only makes it possible to further reduce the longitudinal dimension of the internal space 44, leading to further reduction of the power consumption by the heater 42, but also assures a higher response of the sensing element 2 to a change in the concentration of the combustible gas component of interest of the subject gas. The seventh embodiment of FIG. 11 is different from the fifth embodiment of FIG. 9, in that a pin hole 58 is formed through the proton ion conductive solid electrolyte layer 4g, as the first diffusion control means, in place of the first diffusion control passage 12. The pin hole 58 as the first diffusion control means is advantageous over the passage 12, in that the diameter of the pin hole 58 can be changed even after the firing of the layer 4g, by a drilling operation, for example, for adjusting the diffusion resistance to the nominal value, or reducing a deviation of the diffusion resistance from the nominal value.

Like the first and second electrochemical oxygen pumping cells, the proton pump provided in the fourth through seventh embodiments of FIGS. 5 and 9-11 is preferably operated at a temperature as high as possible. In this sense, it is desirable to position the oxygen and proton pumps at a portion of the sensing element 2 which is held at a relatively high temperature. Generally, the temperature of the portion heated by the heater 42 is suitably determined depending upon the current flowing through the pump circuit. It is also noted that if the voltages to be applied to the proton pump and the oxygen pumps are too high, $H_2O$ in the atmosphere tends to be undesirably decomposed. To prevent this decomposition, too, it is desirable to control the heater 42 to maintain the sensing element 2 at the relatively high operating temperature described above, and lower the impedance of the proton and oxygen pumps, for thereby lowering the voltages to be applied to the proton and oxygen pumps.

It is preferable to provide current detecting means such as an ammeter in a closed circuit which includes the inner and outer proton pumping electrodes 48, 50 and proton pumping power source 52. The proton pumping current detected is proportional to a sum of the CO concentration and the $H_2$ concentration of the subject gas. Therefore, the total concentration of the CO and $H_2$ can be measured simultaneously with the HC concentration.

The proton ion conductive solid electrolyte layer 4g may be formed of a suitable known material such as $LaYO_3$, other than $SrCeO_3$ used in the illustrated embodiments. The aqueous gas converting catalyst layer 56 may be formed of a suitable known material such as $Fe_3O_4$, other than $Cr_2O_3$—$Fe_3O_4$ used in the illustrated embodiments. The aqueous gas converting catalyst layer 56 may consist of a porous ceramic body such as a porous alumina body which contains such a catalyst material as indicated above. The catalyst layer 56 need not be formed on the inner proton pumping electrode 48, but may be disposed at any other suitable position, for example, adjacent to the diffusion control means, between the electrode 48 and the diffusion control means, on an area of the surface of the oxygen ion conductive solid electrolyte layer 4c which is opposed to the electrode 48, or on any other surface area defining the internal space 44 (first or second cavity 6, 8). To promote the catalytic reaction of the aqueous gas converting catalyst layer 56, it is generally desirable to locate the layer 56 at a portion whose temperature does not exceed 600° C., preferably, 500° C.

The sensing element used for the combustible gas component measuring apparatus of the present invention may use a constant-voltage power source 60 for applying a predetermined constant voltage (e.g., 900 mV) to the first electrochemical oxygen pumping cell, as in an eighth embodiment of the invention illustrated in FIG. 12. Unlike the preceding embodiments, the present embodiment of FIG. 12 is adapted such that the voltage to be applied between the inner and outer pumping electrodes 16, 18 is not feedback-controlled on the basis of the output of the first oxygen partial pressure detecting means or first electrochemical sensing cell, but is held constant.

Since it is essential that the oxygen concentration or partial pressure of the atmosphere within the first cavity 6 be controlled to a value so as to inhibit the burning or combustion of the combustible gas components, the voltage to be applied to the two electrodes 16, 18 of the first electrochemical oxygen pumping cell may be held constant (for example, at 900 mV). In this respect, it is noted that the actual voltage between the electrodes 16, 18 will drop from the nominal voltage of the constant-voltage power source 60 by an amount a which depends upon an amount of change of the impedance due to a change in the temperature of the sensing element 2. Therefore, the nominal voltage minus the voltage drop a should be equal to or higher than a desired value corresponding to the oxygen concentration of the atmosphere which is desired to be established in the first cavity 6. In other words, the voltage to be applied between the electrodes 16, 18 should be determined so that the oxygen concentration in the first cavity 6 is not higher than a predetermined upper limit at which the combustible gas components cannot be burned.

While the present invention may be embodied in various forms as explained above by way of example, it is to be understood that the invention may be embodied with various changes, modifications and improvements, which may occur to those skilled in the art, without departing from the spirit and scope of the invention.

In the sensing element 2 of FIGS. 2(a) and 2(b), for example, the internal space 44 is in communication with the external subject gas space through the first diffusion control means 12. However, the space 44 may directly communicate with the external subject gas space at the distal end of the sensing element 2. That is, the first diffusion means 12 may have the same width dimension as the space 44. For improved stability of the atmosphere in the space 44 or for facilitating the control of the atmosphere in the space 44, it is desirable that the cross sectional area of the first diffusion control passage 12 in a plane perpendicular to the length and the top surface of the sensing element 2 be smaller than that of the space 44. In the embodiments of FIGS. 1 and 5, the second diffusion control passage 14 is provided as the second diffusion control means for restricted communication between the first and second cavities 6, 8 under a predetermined diffusion resistance. The provision of this second diffusion control passage 14 is desirable in order to provide a diffusion resistance for restricting the diffusion flow of oxygen between the first and second cavities 6, 8. If the oxygen which has been once pumped into the second cavity 8 by the second electrochemical oxygen pumping cell was discharged into the external subject gas space by the oxygen pumping action of the first electrochemical oxygen pumping cell in the first cavity 6, the discharged amount of oxygen would cause a corresponding amount of detecting error of the apparatus. To prevent the oxygen flow from the second cavity 8 toward the first cavity 6, it is desirable to provide a suitable throttling or diffusion restricting passage between these two cavities 6, 8.

The diffusion coefficient of the second diffusion control means (14) may be made smaller than that of the first diffusion control means (12). In this case, a variation in the pumping current of the second electrochemical oxygen pumping cell due to plugging of the first diffusion control means (12) can be reduced. The first diffusion control means (12) may be plugged by solid substances included in a combustion gas as the subject gas.

The sensing element 2 may be constructed with various other modifications which may occur to those skilled in the art. For instance, a single electrode may be provided in the reference air passage 10, to achieve the functions of the reference electrode 24 and the outer pumping electrode 18 or 30.

The foregoing description of the preferred embodiments of the description refers to HC, CO and $H_2$ as combustible gas components, the method and apparatus according to the principle of the present invention are equally applicable to the measurement of other combustible gas components, provided those combustible gas components or gases produced by decomposition of those components can be oxidized by oxygen and burned. For example, $NH_3$ which is decomposed to produce $N_2$ and $H_2$ may be considered to be a combustible gas component that can be dealt with according to the present invention. The $NH_3$ concentration can be measured in the following manner, by the apparatus using the sensing element 2 constructed according to the first embodiment of FIGS. 1(a) and 1(b), for example.

Initially, the heater 42 is energized to maintain the sensing element 2 at 700° C. In this heating condition, the subject gas including $NH_3$ is introduced into the first cavity 6 through the first diffusion control passage 12. In the first cavity, $NH_3$ is decomposed to produce $N_2$ and $H_2$. At this time, the oxygen partial pressure within the first cavity 6 is held at $10^{-20}$ atm by the first electrochemical oxygen pumping cell, to inhibit oxidization and burning of $H_2$ produced by decomposition of $NH_3$. The atmosphere within the first cavity 6 whose oxygen partial pressure has been controlled and which includes $N_2$ and $H_2$ is introduced into the second cavity 8 through the second diffusion control passage 14. A predetermined voltage is applied between the inner and outer pumping electrodes 28, 30 of the second electrochemical oxygen pumping cell, so as to cause a flow of a pumping current in a direction to effect a pumping action for pumping oxygen from the reference air passage 10 into the second cavity 8. As a result, the $H_2$ produced by decomposition of $KH_3$ reacts with the oxygen introduced in the second cavity 8, whereby $H_2O$ is produced. The pumping current flowing through the second electrochemical oxygen pumping cell at this time corresponds to the amount of oxygen necessary to burn the $H_2$ produced by decomposition of $NH_3$. Therefore, the concentration of $KH_3$ can be determined on the basis of the pumping current measured.

The graph of FIG. 13 indicates a relationship between the pumping current of the second electrochemical oxygen pumping cell detected by the sensing element 2 of the first embodiment, and the $NH_3$ concentration of a specimen gas. Namely, the pumping current was detected by the ammeter 34, at different values (1000 ppm, 2000 ppm, 3000 ppm and 4000 ppm) of the $NH_3$ concentration, while the first and second cavities 6, 8 were both held at 700° C.

Where the subject gas includes combustible gas components other than $NH_3$, the pumping current flowing through the second electrochemical oxygen pumping cell corresponds to a sum of the amount of oxygen necessary to oxidize and burn the combustible gas components other than $NH_3$, and the amount of oxygen necessary to oxidize and burn $H_2$ which was produced as a result of decomposition of $NH_3$. The $NH_3$ concentration of the subject gas in this case can be determined by a difference (Ip1−Ip2), where Ip1 represents the pumping current corresponding to the amount of oxygen necessary to oxidize and burn all of the combustible gas components included in the subject gas, where Ip2 represents the pumping current corresponding to the amount of oxygen necessary to oxidize and burn the combustible gas components other than $NH_3$, namely, all the combustible gas components left after $NH_3$ was removed by bubbling the subject gas in water, for example. The difference (Ip1−Ip2) is equivalent to the pumping current which corresponds to the amount of oxygen necessary to oxidize and burn only the $NH_3$.

What is claimed is:

1. A method of measuring a combustible gas component of a subject gas, comprising the steps of:
   introducing said subject gas into a first processing zone under a predetermined diffusion resistance;
   energizing a first electrochemical oxygen pumping cell to perform an oxygen pumping action for pumping oxygen out of said first processing zone to thereby control an oxygen partial pressure of an atmosphere within said first processing zone to a predetermined value at which said combustible gas component cannot be substantially burned;

introducing the atmosphere from said first processing zone into a second processing zone under a predetermined diffusion resistance;

energizing a second electrochemical oxygen pumping cell to perform an oxygen pumping action for pumping oxygen into said second processing zone to thereby burn said combustible gas component present in an atmosphere within said second processing zone; and detecting one of a pumping current flowing through said second electrochemical oxygen pumping cell and a voltage between electrodes of said second electrochemical oxygen pumping cell during energization of said second electrochemical oxygen pumping cell, and obtaining an amount of said combustible gas component in said subject gas, on the basis of the detected pumping current or voltage.

2. A method according to claim 1, wherein said subject gas includes carbon monoxide, hydrogen and hydrocarbon as combustible gas components, said method further comprising a step of burning said carbon monoxide and hydrogen before said subject gas is introduced into said first processing zone, and wherein said step of obtaining an amount of said combustible gas component comprises determining a concentration of said hydrocarbon in said subject gas, on the basis of said detected pumping current or voltage of -said second electrochemical oxygen pumping cell.

3. A method according to claim 1, wherein said subject gas includes hydrogen and hydrocarbon as combustible gas components, said method further comprising a step of energizing a proton pump to perform a proton pumping action for pumping hydrogen out of said first and second processing zone, and wherein said step of obtaining an amount of said combustible gas component comprises determining a concentration of said hydrocarbon in said subject gas, on the basis of said detected pumping current or voltage of said electrochemical oxygen pumping cell.

4. A method according to claim 1, further comprising a step of detecting said oxygen partial pressure of said atmosphere within said first processing zone, and wherein said step of energizing said first electrochemical oxygen pumping cell comprises controlling a voltage of a variable-voltage power source to be applied to electrodes of said first electrochemical oxygen pumping cell, on the basis of the detected oxygen partial pressure within said first processing zone, such that said detected oxygen partial pressure within said first processing zone is held at said predetermined value.

5. A method according to claim 1, wherein said oxygen partial pressure of the atmosphere within said first processing zone is held at $10^{-14}$ atm or lower.

6. A method according to claim 1, wherein said step of energizing said second electrochemical oxygen pumping cell comprises performing said oxygen pumping action such that an amount of oxygen to be pumped into said second processing zone is not smaller than an amount which is substantially necessary to burn said combustible gas component, and such that a partial pressure of residual oxygen remaining in said second processing zone after burning of said combustible gas component is held at a predetermined value.

* * * * *